(12) United States Patent
Guzaev

(10) Patent No.: US 8,552,175 B2
(45) Date of Patent: *Oct. 8, 2013

(54) SULFUR TRANSFER REAGENTS FOR OLIGONUCLEOTIDE SYNTHESIS

(75) Inventor: Andrei P. Guzaev, Vista, CA (US)

(73) Assignee: A.M. Chemicals, Inc., San Diego, CA (US)

( * ) Notice: Subject to any disclaimer, the term of this patent is extended or adjusted under 35 U.S.C. 154(b) by 152 days.

This patent is subject to a terminal disclaimer.

(21) Appl. No.: 12/958,348

(22) Filed: Dec. 1, 2010

(65) Prior Publication Data

US 2011/0137021 A1 Jun. 9, 2011

Related U.S. Application Data

(63) Continuation-in-part of application No. PCT/US2009/041569, filed on Apr. 23, 2009.

(51) Int. Cl.
| | |
|---|---|
| *C07H 21/00* | (2006.01) |
| *C07D 417/00* | (2006.01) |
| *C07D 513/00* | (2006.01) |
| *C07D 285/14* | (2006.01) |
| *C07D 285/08* | (2006.01) |

(52) U.S. Cl.
USPC .......................... 536/25.34; 548/129; 548/130

(58) Field of Classification Search
None
See application file for complete search history.

(56) References Cited

U.S. PATENT DOCUMENTS

| | | | |
|---|---|---|---|
| 5,852,168 A | 12/1998 | Barany et al. | |
| 6,242,591 B1 | 6/2001 | Cole et al. | |
| 6,500,944 B2 | 12/2002 | Roy et al. | |
| 7,098,325 B2 | 8/2006 | Martin et al. | |
| 7,723,528 B2 * | 5/2010 | Guzaev | 548/123 |
| 2005/0182025 A1 | 8/2005 | Tseng | |

FOREIGN PATENT DOCUMENTS

WO  WO-97/41130  11/1997

OTHER PUBLICATIONS (R) Iyer et al., "The Automated Synthesis of Sulfur-Containing Oligodeoxyribo-nucleotides Using 3H-1,2-Benzodithiol-3-one 1,1-Dioxide as a Sulfur Transfer Agent," Journal of Organic Chemistry, 55(15), 4693-4699 (1990).*
Efimov, V.A. et al., New efficient sulfurizing reagents for the preparation of oligodeoxyribonucleotide phosphorothioate analogues, Nucl. Acids Res. 23, 4029-4033 (1995).
International Search Report dated Nov. 5, 2009 for PCT Application No. PCT/US2009/41569.
Kumar, G. and Poonian, M.S., Improvements in Oligodeoxyribonucleotide Synthesis: Methyl N,N-Dialkyphosphoramidite Dimer Units for Solid Support Phosphite Methodology, J. Org. Chem. 49(25), 4905-12 (1984).
Lemaitre et al, Sulfurizing Reagent II and its Use in Synthesizing Oligonucleotide Phosphorothioates, The Glen Report, Supplementary Material, Dec. 2006, vol. 18, No. 1, pp. 1-6.
Rao, V.M. et al., Dibenzoyl Tetrasulfide 13 A Rapid Sulphur Transfer Agent in the Synthesis of Phosphorothioate Analogues of Oligonucleotides, Tetrahedron Lett. 33, 4839-4842 (1992).
Rao, V.M. and Macfarlane, K., Solid Phase Synthesis of Phosphorothioate Oligonucleotides Using Benzyltriethylammonium Tetrathiomolybdate as a Rapid Sulfur Transfer Reagent, Tetrahedron Lett. 35, 6741-6744 (1994).
Song, Q. and Jones, R.A., Use of Silyl Ethers as Fluoride ion Scavengers in RNA Synthesis, Tetrahedron Lett. 40, 4653-4654 (1999).
Stec, W.J. et al., Bis(O,O-Diisopropoxy Phosphinothioyl) Disulfide 13 A Highly Efficient Sulfurizing Reagent for Cost-Effective Synthesis of Oligo(Nucleoside Phosphorothioate)s Tetrahedron Lett. 33, 5317-5320 (1993).
Usman, N. et al., Automated Chemical Synthesis of Long Oligoribonucleotides Using 2 19-O-Silylated Ribonucleoside 3 19-O-Phosphoramidites on a Controlled-Pore Glass Support: Synthesis of a 43-Nucleotide Sequence Similar to the 3 19-Half Molecule of an *Escherichia coli* Formylmethionine tRNA, J. Am. Chem. Soc. 109, 7845-7854 (1987).
Vu, H. and Hirschbein, B.L., Internucleotide Phosphite Sulfurization With Tetraethyllhiuram Disulfide, Phosphorothioate Oligonucleotide Synthesis Via Phosphoramidte Chemistry, Tetrahedron Lett. 32, 3005-3008 (1991).
Zhang, Z. et al., Solid Phase Synthesis of Oligonucleotide Phosphorothioate Analogues Using 3-Methyl-1,2,4-dithioazolin-5-one (MEDITH) as a New Sulfur-Transfer Reagent, Tetrahedron Lett. 40, 2095-2098 (1999).

* cited by examiner

*Primary Examiner* — Lawrence E Crane
(74) *Attorney, Agent, or Firm* — Kilpatrick Townsend & Stockton LLP

(57) ABSTRACT

The use of N-formamidino-5-amino-3H-1,2,4-dithiazole-3-thiones, 5-phenyl-3H-1,2,4-dithiazole-3-thiones, and derivatives thereof as novel, efficient sulfur-transfer reagents is disclosed. Sulfur transfer from these reagents to compounds containing a P(III) atom (e.g., triphenylphosphine, 5'-O-DMT-thymidine 2-cyanoethyl-(N,N-diisopropyl)phosphoramidite, and 5'-O-DMT-3'-O-levulinyl dithymidilyl 2-cyanoethyl phosphite), was studied in solution by $^{31}$P NMR and HPLC. The sulfur transfer from title compounds was also studied in the solid-phase synthesis of oligonucleotide phosphorothioates by phosphoramidite methods. In this application, the efficiency of the sulfur transfer reaction for 2'-deoxyoligonucleotides was better than 99.5%. The novel sulfurizing agents are synthesized, at low cost, using simple chemical methods. As opposed to many sulfur transfer reagents known in the prior art such as 1,2-benzodithiol-3-one-1,1-dioxide (Beaucage reagent) and 5-ethoxy-3H-1,2,4-dithiazole-2-one (EDIT), the sulfurizing agents disclosed herein are highly stable in solution, which increases their practical and commercial value.

19 Claims, 9 Drawing Sheets

SEQUENCE LISTING

```
<160> NUMBER OF SEQ ID NOS: 5

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttttttttt                                                              10

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgtgagtacc actgattc                                                    18

<210> SEQ ID NO 3
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: 2'-O-methyl-u
<220> FEATURE:
<221> NAME/KEY: modified_base
<222> LOCATION: (2)
<223> OTHER INFORMATION: 2'-O-methyl-g
<220> FEATURE:
```

```
<221> NAME/KEY: modified_base
<222> LOCATION: (3)
<223> OTHER INFORMATION: 2'-O-methyl-u
<220> FEATURE:
<221> NAME/KEY: modified_base
<222> LOCATION: (4)
<223> OTHER INFORMATION: 2'-O-methyl-g
<220> FEATURE:
<221> NAME/KEY: modified_base
<222> LOCATION: (5)
<223> OTHER INFORMATION: 2'-O-methyl-a
<220> FEATURE:
<221> NAME/KEY: modified_base
<222> LOCATION: (14)
<223> OTHER INFORMATION: 2'-O-methyl-g
<220> FEATURE:
<221> NAME/KEY: modified_base
<222> LOCATION: (15)
<223> OTHER INFORMATION: 2'-O-methyl-a
<220> FEATURE:
<221> NAME/KEY: modified_base
<222> LOCATION: (16)..(17)
<223> OTHER INFORMATION: 2'-O-methyl-u
<220> FEATURE:
<221> NAME/KEY: modified_base
<222> LOCATION: (18)
<223> OTHER INFORMATION: 2'-O-methyl-c

<400> SEQUENCE: 3
ugugagtacc actgauuc                                                 18

<210> SEQ ID NO 4
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ugugaguacc acugauuc                                                 18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tagtgaagta cactatgatg t                                             21
```

SULFUR TRANSFER REAGENTS FOR OLIGONUCLEOTIDE SYNTHESIS

CROSS-REFERENCE TO RELATED APPLICATIONS

This application claims priority from PCT Application No. PCT/US2009/041569, filed on Apr. 23, 2009, which claims priority from U.S. application. Ser. No. 12/134,136, filed on Jun. 5, 2008, now issued as U.S. Pat. No. 7,723,528, each of which are hereby incorporated by reference in their entirety.

SEQUENCE LISTING

The instant application contains a Sequence Listing which has been submitted via EFS-Web and is hereby incorporated by reference in its entirety. Said ASCII copy, created on Jun. 25, 2009, is named 48058202.txt and is 2 kilo bytes in size.

BACKGROUND OF THE INVENTION

1. Field of the Invention

The invention relates to the chemical synthesis of oligonucleotides and to chemical entities useful in such synthesis. More specifically, the invention relates to sulfur transfer reagents capable of converting P(III) internucleosidic linkages of oligonucleotides to P(V) phosphorothioate linkages in solution or on solid phase.

2. Summary of the Related Art

Oligonucleotides and modified oligonucleotides are molecular tools of indispensable importance for research in molecular biology and for a variety of diagnostic and pharmaceutical applications including the use of siRNA and antisense inhibition of gene expression. Oligonucleotides that contain unnatural internucleoside linkages where one of the nonbridging oxygen atoms of the phosphate group is replaced by a sulfur atom are referred to as oligonucleotide phosphorothioates. Due to their enhanced nucleolytic stability, oligonucleotide phosphorothioates are among the most commonly used analogues. Their widespread use has led to an increasing demand for expedited, inexpensive, and efficient methods for their preparation.

Synthesis of oligonucleotides is commonly performed on solid phase using well-established protocols employing phosphoramidite or H-phosphonate methods. Briefly, these approaches comprise anchoring the 3'-most nucleoside to a solid support functionalized with amino and/or hydroxyl moieties and subsequently adding the additional nucleotide residues in stepwise fashion. Internucleoside linkages are formed between the 3' functional group of the incoming nucleoside and the 5' hydroxyl group of the 5'-terminal nucleoside of the solid support-bound oligonucleotide. In the phosphoramidite approach, the internucleoside linkage is a protected phosphite moiety, whereas in the H-phosphonate approach, it is an H-phosphonate moiety. To convert these to the sulfur-containing phosphorothioate internucleoside linkage, the phosphite or H-phosphonate moieties are reacted with an appropriate sulfur transfer reagent. In the H-phosphonate approach, this sulfurization is carried out on all of the H-phosphonate linkages in a single step following the completion of oligonucleotide chain assembly, typically using elemental sulfur in a mixture of carbon disulfide and pyridine. In contrast, the phosphoramidite approach allows one to carry out a stepwise sulfurization following each coupling. Currently, the vast majority of oligonucleotides is synthesized using the phosphoramidite approach.

A number of sulfurization agents has been applied to the synthesis of oligonucleotide phosphorothioates. Examples of such agents include:

3H-1,2-benzodithiol-3-one-1,1-dioxide (or Beaucage reagent; Iyer et al., J. Org. Chem. 1990, 55, 4693-4699), tetraethylthiuram disulfide (TETD; Vu et al., Tetrahedron Lett. 1991, 32, 3005-3008), dibenzoyl tetrasulfide (Rao et al., Tetrahedron Lett. 1992, 33, 4839-4842), bis(O,O-diisopropoxyphosphinothioyl)disulfide (Stec et al., Tetrahedron Lett. 1993, 33, 5317-5320), benzyltriethylammonium tetrathiomolybate (Rao et al., Tetrahedron Lett. 1994, 35, 6741-6744), bis(p-toluenesulfonyl)disulfide (Efimov et al., Nucl. Acids Res. 1995, 23, 4029-4033), 3-ethoxy-1,2,4-dithiazoline-5-one (EDITH) and 1,2,4-dithiazolidine-3,5-dione (U.S. Pat. No. 5,852,168), 3-amino-1,2,4-dithiazole-5-thione (U.S. Pat. No. 6,096,881), phenylacetyl disulfide (U.S. Pat. No. 6,242,591), 3-methyl-1,2,4-dithiazolin-5-one (Zhang et al., Tetrahedron Lett. 1999, 40, 2095-2098), 3-phenyl-1,2,4-dithiazoline-5-one (U.S. Pat. No. 6,500,944), and 3-amino-1,2,4-dithiazolidine-5-one (US 2004-559782 20040405).

Many of the above (e.g., the widely used Beaucage reagent and EDITH) are somewhat difficult to synthesize as their hydrolytic stability is rather low. Agents such as tetraethylthiuram disulfide (TETD) display slow reaction kinetics and thus are less convenient in high-throughput and large scale applications. To date, only Beaucage reagent and TETD are commercially available.

BRIEF DESCRIPTION OF THE INVENTION

The invention provides novel sulfur transfer reagents for the preparation of oligonucleotide phosphorothioates. The sulfur transfer reagents according to the invention are inexpensive in manufacturing, stable in storage, and highly efficient in sulfurization.

In a first aspect, the invention provides novel sulfur transfer reagents having the structure according to Formula I:

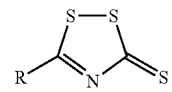

wherein:

R is $-N=C(H)-N(R^1)(R^2)$, $-C_6H_4-R^3$, $-C_6H_3(R^3)(R^4)$; or $-C_6H_2(R^3)(R^4)(R^5)$;

$R^1$ and $R^2$ are independently E, an alkyl group, an aryl group, or an aralkyl group, or $R^1$ and $R^2$ combined form a $-(CH_2)_n-$, wherein n varies from 2 up to about 20, thereby firming a ring structure containing the N to which they are attached, or $R^1+R^2$ combined form the linkage $-(CH_2)_{n'}-X-(CH_2)_{n''}-$, wherein if n' and n'' independently vary from 2 to about 20, and X is O, NR or S, provided, however, that the total of n' and n'' does not exceed 24, and $R^3$, $R^4$ and $R^5$ are independently an alkyl group, an aryl group, an alkoxy croup, an aryloxy group, or a halogen atom, provided, however, that when R is $-C_6H_4-R^3$, $R^3$ is not 2-chloro or 4-chloro, or when R is $-C_6H_3(R^3)(R^4)$, and $R^3$ and $R^4$ are positioned in a 2,4-orientation, $R^3$ and $R^4$ are not both chloro.

The term "alkyl group", as used in this application, refers to a hydrocarbon chain having 1 to about 24 carbon atoms and isomeric forms thereof. Presently preferred alkyl groups have in the range of 1 to about 12 carbon atoms, with alkyl groups having in the range of 1 to about 6 carbon atoms being especially preferred. Presently preferred alkyl groups contemplated for use herein include methyl, ethyl, propyl, 1-methylethyl (isopropyl), butyl, and the like.

The term "aryl group", as used in this application, refers to a monovalent aromatic carbocyclic group of from 6 to about 24 carbon atoms, preferably 6 to about 10 carbon atoms. Presently preferred aryl group is phenyl.

The term "aralkyl group", as used in this application, refers to an aryl group that is attached to another moiety via an alkyl linker. Presently preferred aralkyl group is benzyl.

In one embodiment of the present invention, R of Formula I is —N=C—N(R$^1$)(R$^2$). Compounds according to this embodiment of the present invention have the structure of Formula II, as follows:

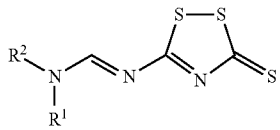

In another embodiment of the present invention, R of Formula I is —N=C(H)—N(R$^1$)(R$^2$) and R$^1$+R$^2$=—(CH$_2$)$_4$—.

In yet another embodiment of the present invention, R of Formula I is —N=C(H)—N(R$^1$)(R$^2$) and R$^1$+R$^2$=—(CH$_2$)$_2$—O—(CH$_2$)$_2$—.

In still another embodiment of the present invention, R of Formula I is —N=C(H)—N(C$_2$H$_5$)$_2$.

In a further embodiment of the present invention, R of Formula I is —N=C(H)—N(C$_4$H$_9$)$_2$.

In a still further embodiment of the present invention, R of Formula I is —C$_6$H$_4$-4-CH$_3$ (i.e., 4-methyl phenyl).

In yet another embodiment of the present invention, R of Formula I is —C$_6$H$_4$-4-OCH$_3$ (i.e., 4-methoxy-phenyl).

In a further embodiment of the present invention, R of Formula I is —C$_6$H$_4$-3-Cl (i.e., 3-chlorophenyl).

In still another embodiment of the present invention, R of Formula I is —C$_6$H$_4$-2-F (i.e., 2-fluorophenyl).

In yet another embodiment of the present invention, R of Formula I is —C$_6$H$_4$-3-F (i.e., 3-fluorophenyl).

In still another embodiment of the present invention, R of Formula I is —C$_6$H$_4$-4-F (i.e., 4-fluorophenyl).

In still another embodiment of the present invention, R of Formula I is —C$_6$H$_3$-2,6-Cl$_2$ (i.e., 2,6-dichlorophenyl).

In yet another embodiment of the present invention, R of Formula I is —C$_6$H$_3$-2,4-F$_2$ (i.e., 2,4-difluorophenyl).

In still another embodiment of the present invention, R of Formula I is —C$_6$H$_3$-2,6-F$_2$ (i.e., 2,6-difluorophenyl).

In yet another embodiment of the present invention, R of Formula I is —C$_6$H$_2$-2,4,6-Cl$_3$ (i.e., 2,4,6-trichlorophenyl).

In still another embodiment of the present invention, R of Formula I is —C$_6$H$_2$-2,4,6-F$_3$ (2,4,6-trifluorophenyl).

In a presently preferred embodiment of the present invention, R of Formula I is —N=C(H)—N(CH$_3$)$_2$.

In another aspect, the invention provides novel processes of sulfur transfer that comprise bringing an oligonucleotide having at least one reactive internucleosidic linkage that contains a phosphorous (III) atom in contact with a solution of a sulfur transfer reagent according to Formula III in a suitable organic solvent for a time sufficient for the transfer of sulfur from said reagent to said reactive internucleosidic linkage, wherein Formula III has the structure:

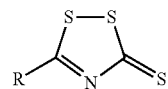

wherein:
R is H, —N=C(H)—N(R$^1$)(R$^2$), —C$_6$H$_4$—R$^3$, —C$_6$H$_3$(R$^3$)(R$^4$); or —C$_6$H$_2$(R$^3$)(R$^4$)(R$^5$);
R$^1$ and R$^2$ are independently H, an alkyl group, an aryl group, or an aralkyl group, or
R$^1$ and R$^2$ combined form a —(CH$_2$)$_n$—, wherein n varies from 2 up to about 20, thereby forming a ring structure containing the N to which they are attached, or
R$^1$+R$^2$ combined form the linkage —(CH$_2$)$_{n'}$—X—(CH$_2$)$_{n''}$—, wherein n' and n" independently vary from 2 to about 20, and X is O, NR or S, provided, however, that the total of n' and n" does not exceed 24, and
R$^3$, R$^4$ and R$^5$ are independently H, an alkyl group, an aryl group, an alkoxy group, an aryloxy group, or a halogen atom.

In one embodiment of the above-described process according to the present invention, R of Formula III is H.

In another embodiment of the above-described process according to the present invention, R of Formula III is —N=C(H)—N(R$^1$)(R$^2$). Compounds according to this embodiment of the present invention have the structure of Formula IV, as follows:

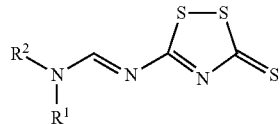

In still another embodiment of the above-described process according to the present invention, R of Formula III is —N=C(H)—N(R$^1$)(R$^2$) and R$^1$+R$^2$=—(CH$_2$)$_4$.

In yet another embodiment of the above-described process according to the present invention, R of Formula III is —N=C(H)—N(R$^1$)(R$^2$) and R$^1$+R$^2$=—(CH$_2$)$_2$—O—(CH$_2$)$_2$—.

In still another embodiment of the above-described process according to the present invention, R of Formula III is —N=C(H)—N(C$_2$H$_5$)$_2$.

In a further embodiment of the above-described process according to the present invention, R of Formula III is —N=C(H)—N(C$_4$H$_9$)$_2$.

In a still further preferred embodiment of the above-described process according to the present invention, R of Formula III is —C$_6$H$_4$-4-CH$_3$ (i.e., 4-methyl phenyl).

In yet another embodiment of the above-described process according to the present invention, R of Formula III is —C$_6$H$_4$-4-OCH$_3$ (i.e., 4-methoxy-phenyl).

In still another embodiment of the above-described process according to the present invention, R of Formula III is —C$_6$H$_4$-2-Cl (i.e., 2-chlorophenyl).

In a further embodiment of the above-described process according to the present invention, R of Formula III is —C$_6$H$_4$-3-Cl (i.e., 3-chlorophenyl).

In yet another embodiment of the above-described process according to the present invention, R of Formula III is —C$_6$H$_4$-4-Cl (i.e., 4-chlorophenyl).

In still another embodiment of the above-described process according to the present invention, R of Formula III is —C$_6$H$_4$-2-F (i.e., 2-fluorophenyl).

In yet another embodiment of the above-described process according to the present invention, R of Formula III is —C$_6$H$_4$-3-F (i.e., 3-fluorophenyl).

In still another embodiment of the above-described process according to the present invention, R of Formula III is —C$_6$H$_4$-4-F (i.e., 4-fluorophenyl).

In yet another embodiment of the above-described process according to the present invention, R of Formula III is —C$_6$H$_3$-2,4-Cl$_2$ (i.e., 2,4-dichlorophenyl).

In still another embodiment of the above-described process according to the present invention, R of Formula III is —C$_6$H$_3$-2,6-Cl$_2$ (i.e., 2,6-dichlorophenyl).

In yet another embodiment of the above-described process according to the present invention, R of Formula III is —C$_6$H$_3$-2,4-F$_2$ (i.e., 2,4-difluorophenyl).

In still another embodiment of the above-described process according to the present invention, R of Formula III is —C$_6$H$_3$-2,6-F$_2$ (i.e., 2,6-difluorophenyl).

In yet another embodiment of the above-described process according to the present invention, R of Formula III is —C$_6$H$_2$-2,4,6-Cl$_3$ (i.e., 2,4,6-trichlorophenyl).

In still another embodiment of the above-described process according to the present invention, R of Formula III is —C$_6$H$_2$-2,4,6-F$_3$ (2,4,6-trifluorophenyl).

In a presently preferred embodiment of the above-described process according to the present invention, R of Formula III is —N=C(H)—N(CH$_3$)$_2$.

In another presently preferred embodiment of the above-described process according to the present invention, R of Formula III is C$_6$H$_5$ (i.e., phenyl).

Suitable organic solvents contemplated for use herein include pyridine, tetrahydrofuran, acetonitrile, N,N-dimethylformamide, N,N-dimethylacetamide, and the like, as well as mixtures of any two or more thereof.

It is presently preferred that sulfur transfer reagents according to the invention be dissolved in a suitable organic solvent at a concentration ranging from about 0.001 up to about 1 M.

It is also presently preferred that sulfur transfer reagents according to the invention be used in a ratio (with respect to the target oligonucleotide) ranging from about 0.67 up to about 20 equivalents.

Sulfur transfer reagents according to the invention are preferably kept in contact with the target oligonucleotide for a period of time ranging from about 5 s up to about 30 min.

Target oligonucleotides contemplated for use herein preferably contain one or more 2'-deoxynucleoside, 2'-O-alkylribonucleoside, 2'-O-protected ribonucleoside, LNA nucleoside residue, or any combination of two or more thereof.

Reactive internucleoside linkages contemplated by invention compounds and methods include phosphites, alkylphosphites, thiophosphites, methylphosphonates, H-phosphonates, H-phosphonothioate internucleosidic linkages, and the like.

In certain presently preferred embodiments of the present invention, the target oligonucleotide contemplated for use herein is attached to a solid phase material.

DETAILED DESCRIPTION OF THE PREFERRED EMBODIMENTS

Figure 1:
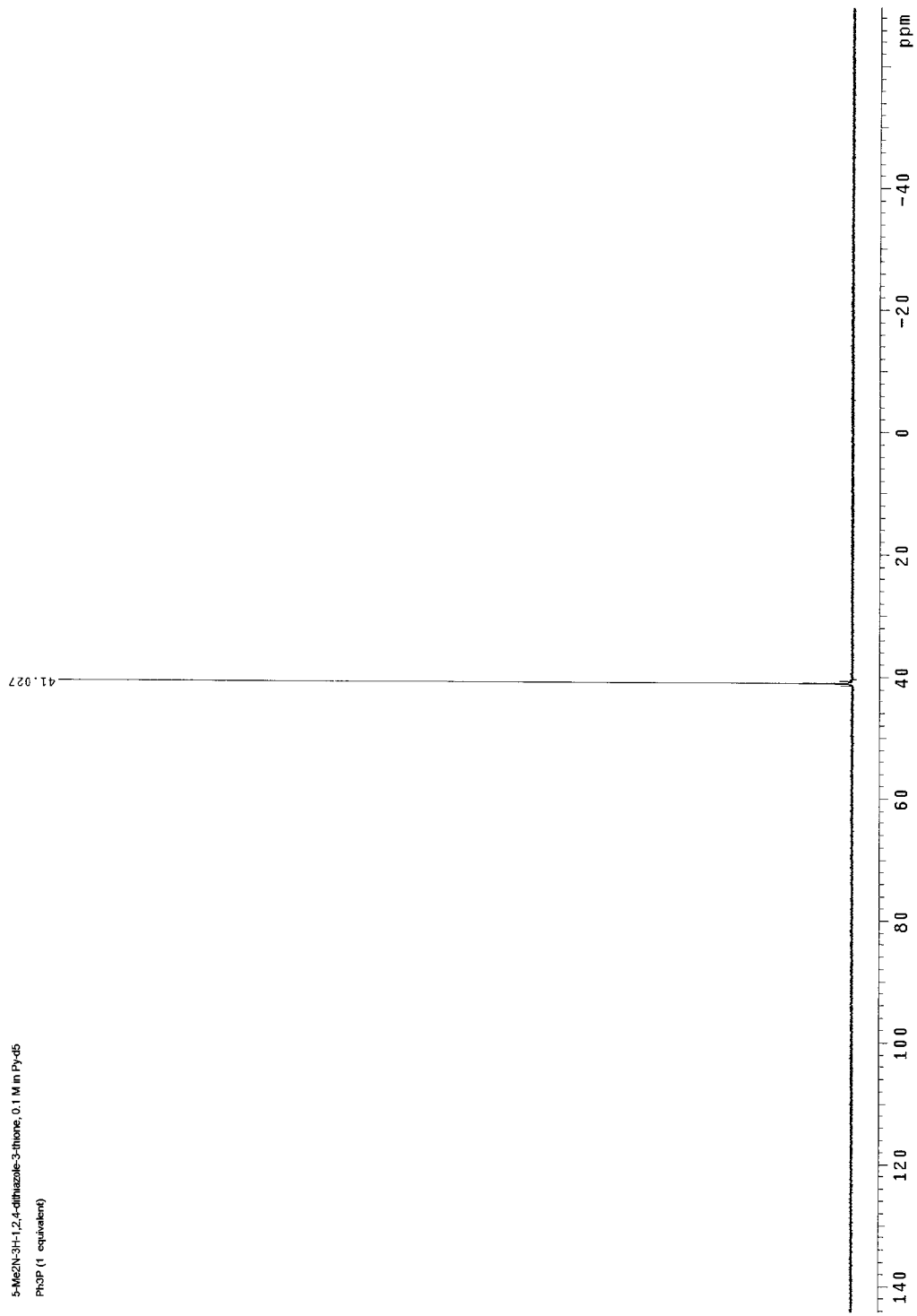
FIG. 1 shows a $^{31}$P NMR spectrum of a mixture formed by equimolecular amounts of N'-(3-thioxo-3H-1,2,4-dithiazol-5-yl)-N,N-dimethylmethanimidamide (Compound 1; see Example 2) and Ph$_3$P (0.1 M in Py-d$_5$).

The invention relates to the chemical synthesis of oligonucleotides and to chemical entities useful in such synthesis. More specifically, the invention relates to sulfur transfer reagents capable of converting P(III) internucleosidic linkages of oligonucleotides to phosphorothioate linkages in solution or on solid phase. The patents and publications cited in this specification are well-known to those skilled in the art and are hereby incorporated by reference in their entirety.

The invention provides novel sulfur transfer reagents for the preparation of oligonucleotide phosphorothioates and processes for such preparation. The sulfur transfer reagents according to the invention are highly efficient. These compounds are inexpensive to manufacture and are stable in the solid state or in solution over an extensive period of time.

In the first aspect, the invention provides novel sulfur transfer reagents having the structure according to Formula I:

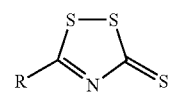

wherein:
R is —N=C(H)—N(R$^1$)(R$^2$), —C$_6$H$_4$—R$^3$, —C$_6$H$_3$(R$^3$)(R$^4$); or —C$_6$H$_2$(R$^3$)(R$^4$)(R$^5$);
R$^1$ and R$^2$ are independently H, an alkyl group, an aryl group, or an aralkyl group, or
R$^1$ and R$^2$ combined form a —(CH$_2$)$_n$—, wherein n varies from 2 up to about 20, thereby forming a ring structure containing the N to which they are attached, or
R$^1$+R$^2$ combined form the linkage —(CH$_2$)$_{n'}$—X—(CH$_2$)$_{n''}$—, wherein n' and n'' independently vary from 2 to about 20, and X is O, NR or S, provided, however, that the total of n' and n" does not exceed 24, and R³, R⁴ and R⁵ are independently an alkyl group, an aryl group, an alkoxy group, an aryloxy group, or a halogen atom, provided, however, that when R is —C₆H₄—R³, R³ is not 2-chloro or 4-chloro, or when R is —C₆H₃(R³)(R⁴), and R³ and R⁴ are positioned in a 2,4-orientation, R³ and R⁴ are not both chloro.

In a presently preferred embodiment of the present invention, R of Formula I is —N=C(H)—N(R¹)(R²), and R¹+R² is —(CH₂)₄—.

In another presently preferred embodiment of the present invention, R of Formula I is —=C(H)—N(R¹)(R²), R¹+R² is —(CH₂)₂—O—(CH₂)₂—.

In yet another presently preferred embodiment of the present invention, R of Formula I is —N=C(H)—N(R¹)(R²), and R¹ and R² are both C₂H₅, such that R of Formula I is —N=C(H)—N(C₂H₅)₂.

In still another presently preferred embodiment of the present invention, R of Formula I is —N=C(H)—N(R¹)(R²), and R¹ and R² are both n-butyl, such that R of Formula I is —N=C(H)—N(C₄H₉)₂.

In a further presently preferred embodiment of the present invention, R of Formula I is —C₆H₄-4-CH₃.

In yet another presently preferred embodiment of the present invention, R of Formula I is —C₆H₄-4-OCH₃ (i.e., 4-methoxy-phenyl).

In a further presently preferred embodiment of the present invention, R of Formula I is —C₆H₄-3-Cl (i.e., 3-chlorophenyl).

In still another presently preferred embodiment of the present invention, R of Formula I is —C₆H₄-2-F (i.e., 2-fluorophenyl).

In yet another presently preferred embodiment of the present invention, R of Formula I is —C₆H₄-3-F (i.e., 3-fluorophenyl).

In still another presently preferred embodiment of the present invention, R of Formula I is —C₆H₄-4-F (i.e., 4-fluorophenyl).

In still another presently preferred embodiment of the present invention, R of Formula I is —C₆H₃-2,6-Cl₂ (i.e., 2,6-dichlorophenyl).

In yet another presently preferred embodiment of the present invention, R of Formula I is —C₆H₃-2,4-F₂ (i.e., 2,4-difluorophenyl).

In still another presently preferred embodiment of the present invention, R of Formula I is —C₆H₃-2,6-F₂ (i.e., 2,6-difluorophenyl).

In yet another presently preferred embodiment of the present invention, R of Formula I is —C₆H₂-2,4,6-Cl₃ (i.e., 2,4,6-trichlorophenyl).

In still another presently preferred embodiment of the present invention, R of Formula I is —C₆H₂-2,4,6-F₃ (2,4,6-trifluorophenyl).

In another aspect of the present invention, there are provided novel processes of sulfur transfer that comprise bringing an oligonucleotide having at least one reactive internucleosidic linkage that contains a phosphorous (III) atom in contact with a solution of a sulfur transfer reagent according to Formula III in an organic solvent for a time sufficient for the transfer of sulfur from said reagent to said reactive internucleosidic linkage, wherein Formula III has the structure:

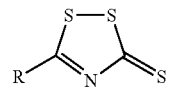

wherein:
R is H, —N=C(H)—N(R¹)(R²), —C₆H₄—R³, —C₆H₃(R³)(R⁴); or —C₆H₂(R³)(R⁴)(R⁵);

R¹ and R² are independently H, an alkyl group, an aryl group, or an aralkyl group, or R¹ and R² combined form a —(CH₂)ₙ—, wherein n varies from 2 up to about 20, thereby forming a ring structure containing the N to which they are attached, or R¹+R² combined form the linkage —(CH₂)ₙ'—X—(CH₂)ₙ"—, wherein n' and n" independently vary from 2 to about 20, and X is O, NR or S, provided, however, that the total of n' and n" does not exceed 24, and R³, R⁴ and R⁵ are independently H, an alkyl group, an aryl group, an alkoxy group, an aryloxy group, or a halogen atom.

In one presently preferred embodiment of the above-described process according to the present invention, R of Formula III is H.

In another presently preferred embodiment of the above-described process according to the present invention, R of Formula III is —N=C(H)—N(R¹)(R²). Compounds according to this embodiment of the present invention have the structure of Formula IV, as follows:

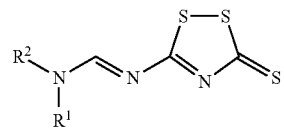

In still another presently preferred embodiment of the above-described process according to the present invention, R of Formula III is —N=C(H)—N(R¹)(R²) and R¹+R²=—(CH₂)₄—.

In yet another presently preferred embodiment of the above-described process according to the present invention, R of Formula III is —N=C(H)—N(R¹)(R²) and R¹+R²=—(CH₂)₂—O—(CH₂)₂—.

In still another presently preferred embodiment of the above-described process according to the present invention, R of Formula III is —N=C(H)—N(C₂H₅)₂.

In a further presently preferred embodiment of the above-described process according to the present invention, R of Formula III is —N=C(H)—N(C₄H₉)₂.

In a still further presently preferred embodiment of the above-described process according to the present invention, R of Formula III is —C₆H₄-4-CH₃ (i.e., 4-methyl phenyl).

In yet another presently preferred embodiment of the above-described process according to the present invention, R of Formula III is —C₆H₄-4-OCH₃ (i.e., 4-methoxy-phenyl).

In still another presently preferred embodiment of the above-described process according to the present invention, R of Formula III is —C₆H₄-2-Cl (i.e., 2-chlorophenyl).

In a further presently preferred embodiment of the above-described process according to the present invention, R of Formula III is —C₆H₄-3-Cl (i.e., 3-chlorophenyl).

In yet another presently preferred embodiment of the above-described process according to the present invention, R of Formula III is —C₆H₄-4-Cl (i.e., 4-chlorophenyl).

In still another presently preferred embodiment of the above-described process according to the present invention, R of Formula III is —$C_6H_4$-2-F (i.e., 2-fluorophenyl).

In yet another presently preferred embodiment of the above-described process according to the present invention, R of Formula III is —$C_6H_4$-3-F (i.e., 3-fluorophenyl).

In still another presently preferred embodiment of the above-described process according to the present invention, R of Formula III is —$C_6H_4$-4-F (i.e., 4-fluorophenyl).

In yet another presently preferred embodiment of the above-described process according to the present invention, R of Formula III is —$C_6H_3$-2,4-$Cl_2$ (i.e., 2,4-dichlorophenyl).

In still another presently preferred embodiment of the above-described process according to the present invention, R of Formula III is —$C_6H_3$-2,6-$Cl_2$ (i.e., 2,6-dichlorophenyl).

In yet another presently preferred embodiment of the above-described process according to the present invention, R of Formula III is —$C_6H_3$-2,4-$F_2$ (i.e., 2,4-difluorophenyl).

In still another presently preferred embodiment of the above-described process according to the present invention, R of Formula III is —$C_6H_3$-2,6-$F_2$ (i.e., 2,6-difluorophenyl).

In yet another presently preferred embodiment of the above-described process according to the present invention, R of Formula III is —$C_6H_2$-2,4,6-$Cl_3$ (i.e., 2,4,6-trichlorophenyl).

In still another presently preferred embodiment of the above-described process according to the present invention, R of Formula III is —$C_6H_2$-2,4,6-$F_3$ (2,4,6-trifluorophenyl).

In yet another presently preferred embodiment of the above-described process according to the present invention, R of Formula III is —N=C(H)—N($CH_3$)$_2$.

In still another presently preferred embodiment of the above-described process according to the present invention, R of Formula III is $C_6H_5$ (i.e., phenyl).

Organic solvents contemplated for use herein include pyridine, tetrahydrofuran, acetonitrile, N,N-dimethylformamide, N,N-dimethylacetamide, and the like, as well as mixtures of any two or more thereof.

Sulfur transfer reagents according to the present invention are typically dissolved in an organic solvent at a concentration falling in the range of about 0.001 up to about 1 M.

The ratio of sulfur transfer reagent according to the invention, relative to the oligonucleotide to be reacted therewith can vary widely, typically ranging from about 0.67 up to about 20 equivalents.

Sulfur transfer reagent according to the present invention is typically maintained in contact with oligonucleotide to be reacted therewith for a period of time sufficient to achieve the desired transfer of sulfur thereto, with contact times typically ranging from about 5 seconds up to about 30 minutes.

Preferably, oligonucleotides contemplated for use herein contain one or more of 2'-deoxynucleosides, 2'-O-alkylribonucleosides, 2'-O-protected ribonucleosides, LNA nucleoside residues, or the like, or combinations of any two or more thereof.

Preferably, the reactive internucleoside linkage is a phosphite, an alkylphosphite, a thiophosphite, a methylphosphonate, an H-phosphonate, or a H-phosphonothioate internucleosidic linkage.

In a presently preferred embodiment of the present invention, the oligonucleotide contemplated for use herein is attached to a solid phase material.

Compounds 1-19 may be readily synthesized from commercially available starting materials, as disclosed in Schemes 1, 2 and 3, as follows:

Scheme 1:

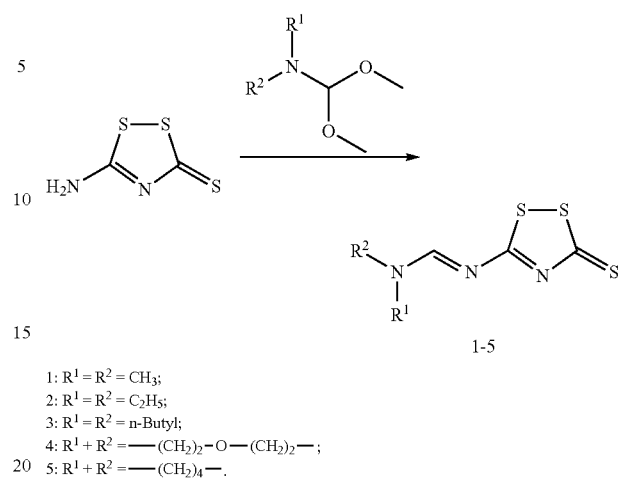

1: $R^1 = R^2 = CH_3$;
2: $R^1 = R^2 = C_2H_5$;
3: $R^1 = R^2$ = n-Butyl;
4: $R^1 + R^2$ = —($CH_2$)$_2$—O—($CH_2$)$_2$—;
5: $R^1 + R^2$ = —($CH_2$)$_4$—.

For example, to synthesize compound 1,3-amino-3H-1,2,4-dithiazole-5-thione (TCI America) was dissolved in DMF and treated with dimethylformamide dimethylacetal (Alfa Aesar, Ward Hill, Mass.) at room temperature (see Scheme 1), followed by precipitation of the product with ethyl ether to give the desired 1 in more than 84% yield and high purity.

Scheme 2:

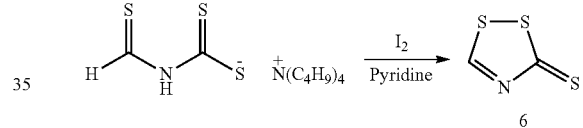

To synthesize compound 6, tetra-n-butylammonium-N-thionoformyldithiocarbamate (prepared as disclosed in the literature, see Gerner, R., Gattow, G. Chalcogenolates. 151. Studies on derivatives of N-thioformyl dithiocarbamic acid. 1. Synthesis and properties of N-thioformyldithiocarbamates. Z. Anorg. Allgem. Chem. 1985, 524, 122-136) was treated with a solution of iodine in the presence of pyridine as illustrated in Scheme 2.

Scheme 3.

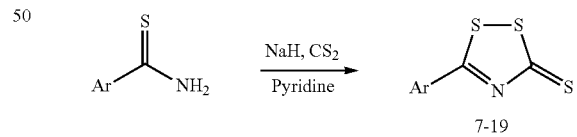

7: Ar = $C_6H_5$;
8: Ar = $C_6H_4$-4-$CH_3$;
9: Ar = $C_6H_4$-4-$OCH_3$;
10: Ar = $C_6H_4$-2-Cl;
11: Ar = $C_6H_4$-3-Cl;
12: Ar = $C_6H_4$-4-Cl;
13: Ar = $C_6H_4$-2-F;
14: Ar = $C_6H_4$-3-F;
15: Ar = $C_6H_4$-4-F;
16: Ar = $C_6H_4$-2,4-$Cl_2$;
17: Ar = $C_6H_4$-2,4-$F_2$;
18: Ar = $C_6H_4$-2,4,6-$Cl_3$;
19: Ar = $C_6H_4$-2,4,6-$F_3$.

To obtain compounds 7-19, the respective thiobenzamides (available commercially for example, from VWR International, West Chester, Pa., or prepared as described in the literature (Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-5330) were treated with NaH and carbon disulfide as illustrated in Scheme 3.

Stability and solubility studies of the sulfur transfer reagent 1 were carried out. As described in greater detail below, Compound 1 was soluble in mixtures of $CH_3CN$ and pyridine, tetrahydrofuran and pyridine, and pyridine alone to concentrations sufficient for performing their function. Compound 1 was stable in mixtures of $CH_3CN$ and pyridine and pyridine alone for more than 20 weeks. Over the test period, no precipitate was deposited from the solutions. In the functional test, Compound 1 did not show any deterioration of the ability to transfer sulfur to solid support-bound internucleosidic phosphite triesters.

Figure 3:
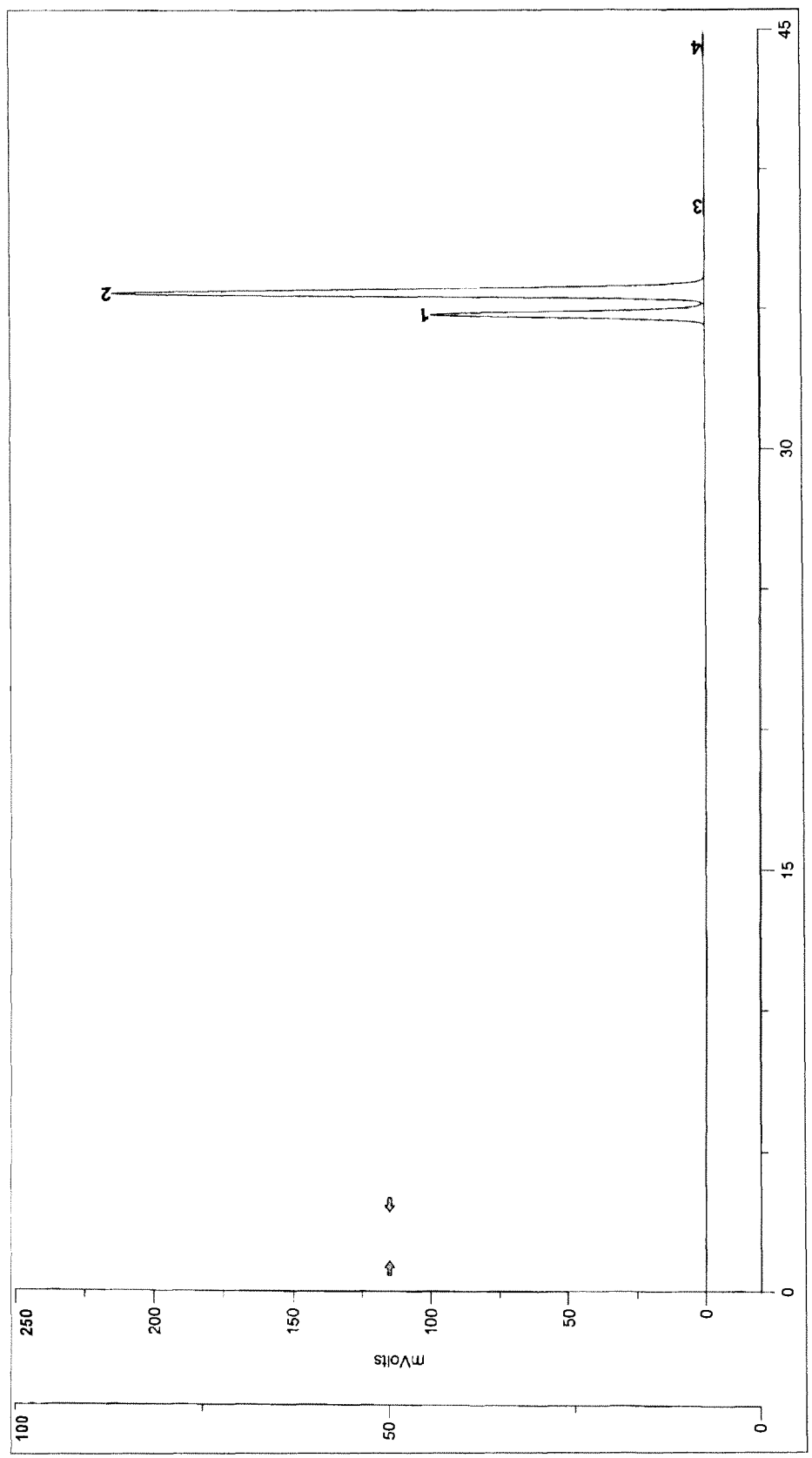
FIG. 3 shows a HPLC profile of a mixture formed by equimolecular amounts of Compound 1 and 5'-O-(4,4'-dimethoxytrityl)-3'-O-levulinyl dithymidyl 2-cyanoethyl phosphite (see Example 23).

The efficiency of these new sulfur-transfer reagents was first evaluated by mixing equimolecular amounts of 1-19 with triphenylphosphine in pyridine-d5 and monitoring the progress of the reaction by $^{31}P$ NMR (see Scheme 4 and FIGS. 1 and 3).

Scheme 4:

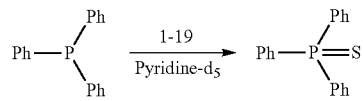

With all of compounds 1-19, the substrate disappeared quantitatively in less than 5 min to give triphenylphosphine sulfide in more than 99% yield plus triphenylphosphine oxide (<0.1%). The stoichiometry of the sulfur transfer was determined by mixing aliquots of 1 with aliquots of triphenylphosphine (1 to 5 equivalents). It was found that two equivalents of compound 1 is capable of producing 3 equivalents of triphenylphosphine sulfide.

Figure 2:
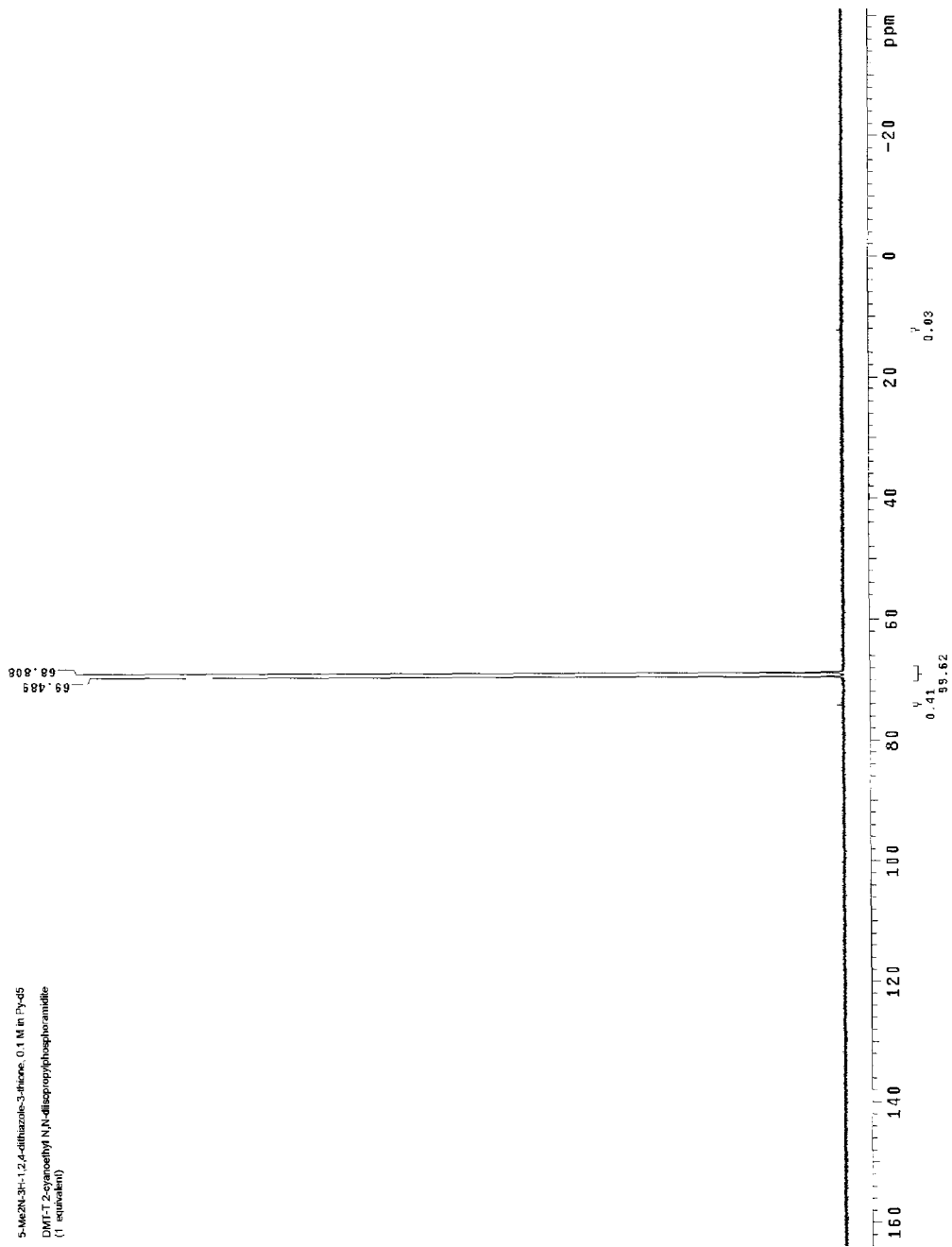
FIG. 2 shows a $^{31}$P NMR spectrum of a mixture formed by equimolecular amounts of Compound 1 and 5'-O-(4,4'-dimethoxytrityl)thymidine 2-cyanoethyl-(N,N-diisopropyl) phosphoramidite 20 (see Scheme 5) (0.1 M in Py-d$_5$).

In a similar manner, compound 1 was reacted with an equimolecular amount of 5'-O-(4,4'-dimethoxytrityl)thymidine 2-cyanoethyl 3'-O—(N,N-diisopropyl)phosphoramidite 20 (see Scheme 5) to give thionophosphoramidate 21 as a mixture of diastereomers in more than 99.9% yield as judged by $^{31}P$ NMR (see FIG. 2).

Scheme 5:

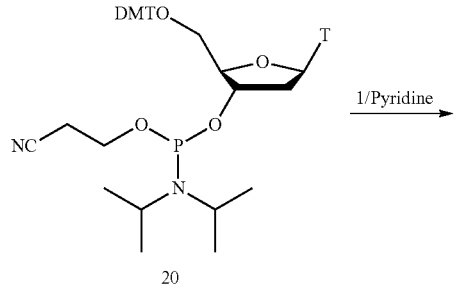

20

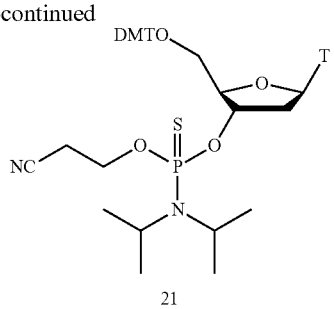

21

To further evaluate the usefulness of Compound 1 as a sulfur transfer reagent, a protected dithymidilyl monophosphorothioate 24 was synthesized by reacting phosphoramidite 20 with 3'-O-levulinylthymidine 22 in the presence of 1H-tetrazole (see Scheme 6).

Scheme 6: Synthesis of compound 24.

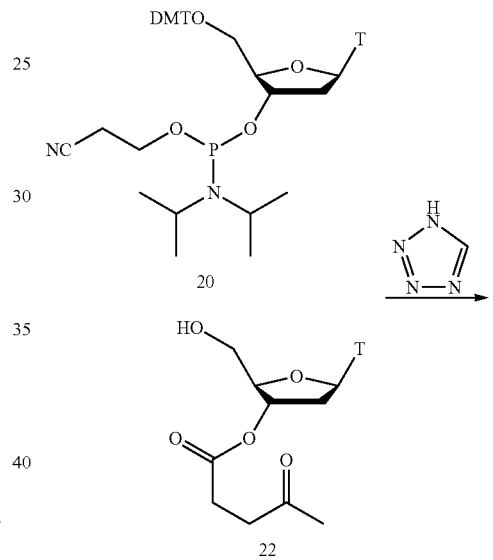

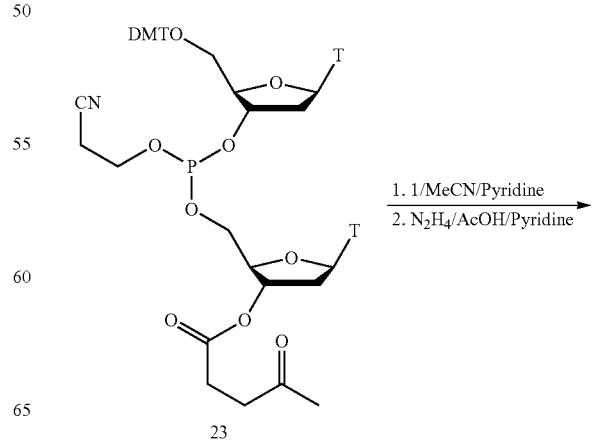

23

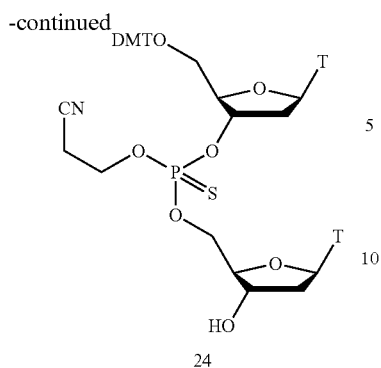

24

Figure 4:
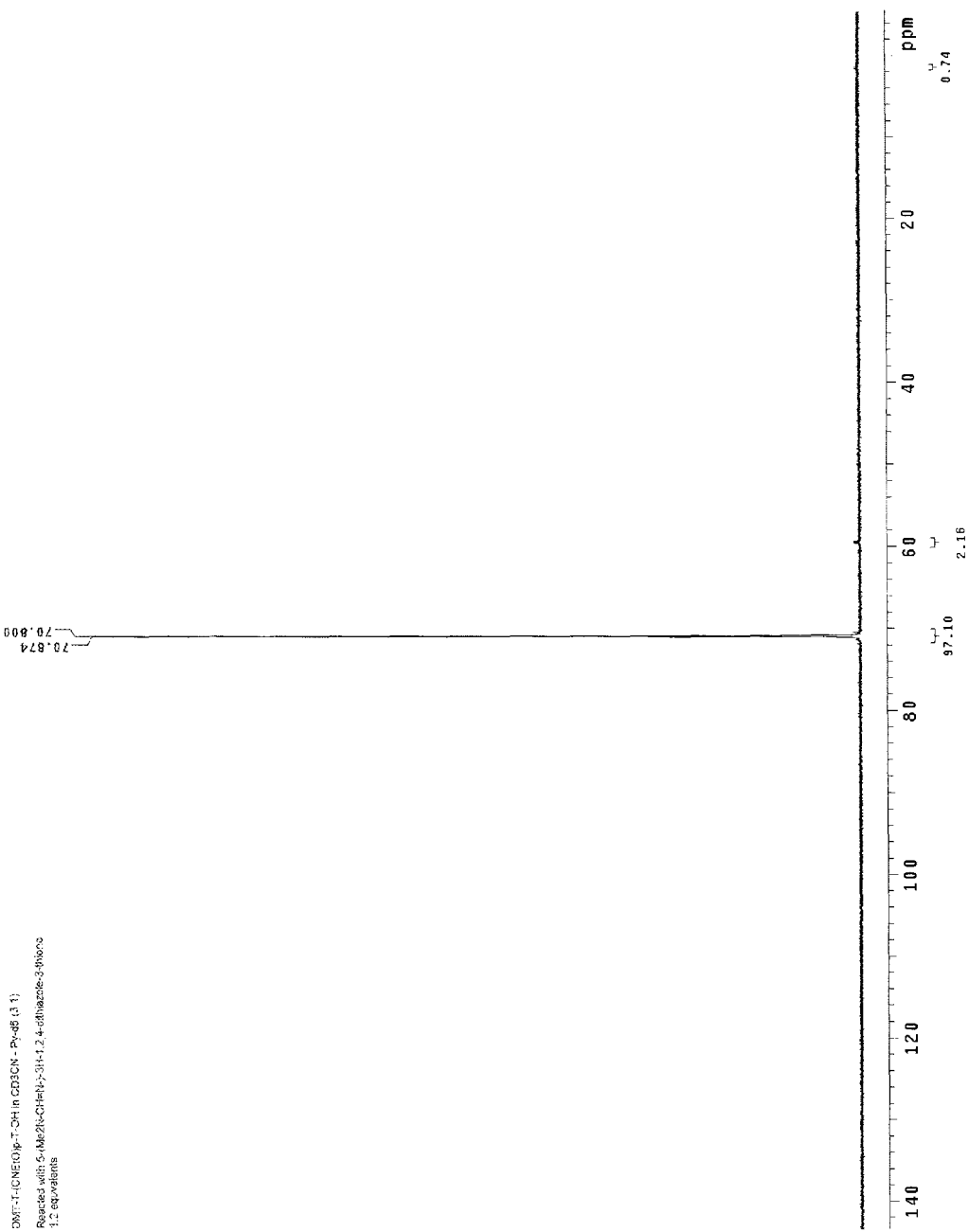
FIG. 4 shows a $^{31}$P NMR spectrum of a mixture formed by equimolecular amounts of Compound 1 and 5'-O-(4,4'-dimethoxytrityl)-3'-O-levulinyl dithymidyl 2-cyanoethyl phosphite (see Example 23) (in CD$_3$CN-Py-d$_5$ (3:1)).

Without isolation, the protected phosphite triester 23 was treated with 1.2 molar excess of 1, and 3'-levulinyl protecting group was removed by further treatment with hydrazinium acetate in a mixture of pyridine and acetic acid. Upon aqueous work-up, compound 24 was analyzed by $^{31}$P NMR and reverse-phase HPLC (see FIGS. 4 and 5, respectively). The results showed that the efficiency of the sulfur transfer was better than 99.3%.

Finally, the usefulness of Compound 1, 7, 12, 17 and 18 as efficient sulfur transfer reagents was evaluated in a solid phase synthesis of oligonucleotides:

DMT-T$_2$ phosphorothioate,

DMT-T$_{10}$ phosphorothioate (SEQ ID NO: 1) and

DMT-d(5'-TGT GAG TAC CAC TGA TTC-3') phosphorothioate (SEQ ID NO:2).

The oligonucleotides were synthesized on 0.2 µmol scale using the following standard protocol for chain assembly:

0.02 to 0.05 M solutions of 1 in appropriate mixtures of CH$_3$CN and pyridine, and 0.5, 1, or 2 min sulfurization time in each synthetic cycle.

Under optimized conditions, the complete sulfur transfer using 0.02, 0.05, and 0.1 M solutions of 1 requires contact times of 2, 1, and 0.5 min, respectively.

After the solid-phase-bound material was released and the protecting groups were removed with concentrated aqueous ammonium hydroxide, the crude oligonucleotide phosphorothioates were analyzed by reverse-phase HPLC and ES MS (FIGS. 6-9). The results show that more than 99.5% sulfur transfer efficiency was achieved at each step, and a yield better than 80% has been achieved in these syntheses. Compounds 7, 12, 17 and 18 demonstrated substantially similar performance in oligonucleotide synthesis.

Accordingly, the efficient preparation of oligonucleotide phosphorothioates by phosphoramidite synthesis in solution and on solid phase using compounds 1-19 as sulfur transfer reagents has been demonstrated. Compounds 1-19 can be synthesized, at low cost, using simple chemical methods. As opposed to many sulfur transfer reagents known in the art such as 3H-1,2-benzodithiol-3-one-1,1-dioxide (Beaucage reagent as disclosed in Beaucage, S. L.; Regan, J. B.; Iyer, R. P. Sulfuration of oligonucleotides by benzodithiole analogs. U.S. Pat. Appl. (1990), 35 pp. US 415710 A0) and 5-ethoxy-3H-1,2,4-dithiazole-2-one (EDIT as disclosed in Barany, G.; Musier-Forsyth, K.; Xu, Q.; Chen, L.; Hammer, R. P. Sulfuration of DNA and RNA using disulfide-containing five-membered heterocycles. PCT Int. Appl. (1997), 130 pp. WO 9741130 A2), compounds 1-19 are highly stable in solution, which increases their practical and commercial value.

EXAMPLES

The following examples are intended to further illustrate certain preferred embodiments of the invention and are not intended to be limiting in nature.

Example 1

General Information

N,N-Dimethylformamide dimethylacetal was obtained from Alfa Aesar (Ward Hill, Mass.). 3-Amino-1,2,4-dithiazole-5-thione was purchased from TCI America. DMT-T-CPG, DMTdC-CPG, 5'-DMT-thymidine cyanoethyl phosphoramidite 6, other deoxynucleoside phosphoramidites, Cap A, Cap B, activator, oxidizing and deblock solutions were purchased from Glen Research, (Sterling, Va.). Anhydrous pyridine, CH$_3$CN and CH$_2$Cl$_2$, and all other chemicals were purchased from Aldrich (Milwaukee, Wis.).

Example 2

N'-(3-thioxo-3H-1,2,4-dithiazol-5-yl)-N,N-dimethylmethanimidamide (1)

Dimethylformamide dimethylacetal (154.2 g, 1.29 mol) was added dropwise to a stirred solution of 5-amino-3H-1,2,4-dithiazole-5-thione (185.2 g, 1.23 mol) in anhydrous DMF (700 mL) over 30 min at 20-25° C. The reaction mixture was stirred at room temperature for 5 h, and ether (600 mL) was slowly added. The precipitate was filtered off, washed on the filter with ether (3×200 mL), and dried in vacuo to give 213.9 g (84.5%) of the title compound 1 as a lemon-yellow crystalline material.

Example 3

N'-(3-thioxo-3H-1,2,4-dithiazol-5-yl)-N,N-diethylmethanimidamide (2)

Following the procedure disclosed in Example 2, compound 2 was prepared from 3H-1,2,4-dithiazole-5-thione (3.0 g, 20 mol) and diethylformamide dimethylacetal (3.09 g, 21 mmol) in 84% yield.

Example 4

N'-(3-thioxo-3H-1,2,4-dithiazol-5-yl)-N,N-dibutylmethanimidamide (3)

Following the procedure disclosed in Example 2, compound 3 was prepared from 3H-1,2,4-dithiazole-5-thione (3.0 g, 20 mol) and dibutylformamide dimethylacetal (4.27 g, 21 mmol) in 75% yield.

Example 5

N'-(3-thioxo-3H-1,2,4-dithiazol-5-yl)-N-pyrrolidinomethanimidamide (4)

Following the procedure disclosed in Example 2, compound 4 was prepared from 3H-1,2,4-dithiazole-5-thione (3.0 g, 20 mol) and dimethylacetal of N-formylpyrrolidine (3.19 g, 22 mmol) in 81% yield.

Example 6

N'-(3-thioxo-3H-1,2,4-dithiazol-5-yl)-N-morpholinomethanimidamide (5)

Following the procedure disclosed in Example 2, compound 5 was prepared from 3H-1,2,4-dithiazole-5-thione (3.0 g, 20 mol) and dimethylacetal of N-formylmorpholine (3.55 g, 22 mmol) in 74% yield.

Example 7

3H-1,2,4-dithiazol-3-thione (6)

Tetra-n-butylammonium-N-thionoformyldithiocarbamate was prepared as disclosed in Gerner, R., Gattow, G. Chalcogenolates. 151. Studies on derivatives of N-thioformyldithiocarbamic acid. 1. Synthesis and properties of N-thioformyldithiocarbamates. *Z. Anorg. Allgem. Chem.* 1985, 524, 122-136. Solutions of tetra-n-butylammonium-N-thionoformyldithiocarbamate (37.9 g, 0.1 mol) in dichloromethane (1.5 L) and of iodine (22.8 g, 0.09 mol) in THF (500 mL) were added simultaneously to the stirred mixture of pyridine (7.4 g, 0.09 mol) and dichloromethane (1.5 L) at room temperature. The mixture was stirred for 30 min, and the solvent was evaporated. The residue was extracted with ether, and the ethereal extract was evaporated. The recovered solid was recrystallized from dichloroethane to give the title compound 6 (4.75 g, 39%), m.p. 73-75° C.

Example 8

5-Phenyl-3H-1,2,4-dithiazol-3-thione (7)

A solution of thiobenzamide (100 g, 0.74 mol, Alfa Aesar, Ward Hill, Mass.) was added dropwise to a stirred suspension of NaH (22 g, 0.74 mol, 60% suspension in mineral oil) in pyridine (1 L) at −15° C. followed by the addition of carbon disulfide (122 g, 1.6 mol). The reaction mixture was stirred for 3 h at −10° C. and the solvent was evaporated. The residue was treated with ether, the solution was removed, and the insoluble material was treated in water (1 L). The precipitate was filtered off, and the clear solution was cooled to 0-4° C. and acidified with dilute hydrochloric acid. The crystalline precipitate was collected, washed with water, and dried to yield compound 7 (37.5 g, 24%).

Example 9

5-(4-Methylphenyl)-3H-1,2,4-dithiazol-3-thione (8)

Following the procedure described in Example 8, compound 8 was prepared from 4-methylbenzenecarbothioamide (3.02 g, 20 mol), NaH (0.48 g, 20 mmol, 60% suspension in mineral oil), and carbon disulfide (3.35 g, 44 mmol) in 25% yield.

Example 10

5-(4-Methoxyphenyl)-3H-1,2,4-dithiazol-3-thione (9)

Following the procedure described in Example 8, compound 9 was prepared from 4-methoxybenzenecarbothioamide (3.35 g, 20 mol), NaH (0.48 g, 20 mmol, 60% suspension in mineral oil), and carbon disulfide (3.35 g, 44 mmol) in 21% yield.

Example 11

5-(2-Chlorophenyl)-3H-1,2,4-dithiazol-3-thione (10)

Following the procedure described in Example 8, compound 10 was prepared from 2-chlorobenzenecarbothioamide (3.43 g, 20 mol; obtained as described in the literature—see Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-5330), NaH (0.48 g, 20 mmol, 60% suspension in mineral oil), and carbon disulfide (3.35 g, 44 mmol) in 28% yield.

Example 12

5-(3-Chlorophenyl)-3H-1,2,4-dithiazol-3-thione (11)

Following the procedure described in Example 8, compound 11 was prepared from 3-chlorobenzenecarbothioamide (3.43 g, 20 mol; obtained as disclosed in the literature—see Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-5330), NaH (0.48 g, 20 mmol, 60% suspension in mineral oil), and carbon disulfide (3.35 g, 44 mmol) in 25% yield.

Example 13

5-(4-Chlorophenyl)-3H-1,2,4-dithiazol-3-thione (12)

Following the procedure described in Example 8, compound 12 was prepared from 4-chlorobenzenecarbothioamide (3.43 g, 20 mol; obtained as described in the literature—see Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-5330.), NaH (0.48 g, 20 mmol, 60% suspension in mineral oil), and carbon disulfide (3.35 g, 44 mmol) in 30% yield.

Example 14

5-(2-Fluorophenyl)-3H-1,2,4-dithiazol-3-thione (13)

Following the procedure described in Example 8, compound 13 was prepared from 2-fluorobenzenecarbothioamide (3.q g, 20 mol; obtained as described in the literature—see Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-5330), NaH (0.48 g, 20 mmol, 60% suspension in mineral oil), and carbon disulfide (3.35 g, 44 mmol) in 28% yield.

Example 15

5-(3-Fluorophenyl)-3H-1,2,4-dithiazol-3-thione (14)

Following the procedure described in Example 8, compound 14 was prepared from 3-fluorobenzenecarbothioamide (3.1 g, 20 mol; obtained as described in the literature—see Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-

5330), NaH (0.48 g, 20 mmol, 60% suspension in mineral oil), and carbon disulfide (3.35 g, 44 mmol) in 25% yield.

Example 16

5-(4-Fluorophenyl)-3H-1,2,4-dithiazol-3-thione (15)

Following the procedure described in Example 8, compound 15 was prepared from 4-fluorobenzenecarbothioamide (3.1 g, 20 mol; obtained as described in the literature—see Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-5330), NaH (0.48 g, 20 mmol, 60% suspension in mineral oil), and carbon disulfide (3.35 g, 44 mmol) in 34% yield.

Example 17

5-(2,4-Dichlorophenyl)-3H-1,2,4-dithiazol-3-thione (16)

Following the procedure described in Example 8, compound 16 was prepared from 2,4-dichlorobenzenecarbothioamide (4.12 g, 20 mol; obtained as described in the literature—see Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-5330), NaH (0.48 g, 20 mmol, 60% suspension in mineral oil), and carbon disulfide (3.35 g, 44 mmol) in 38% yield.

Example 18

5-(2,4-Difluorophenyl)-3H-1,2,4-dithiazol-3-thione (17)

Following the procedure described in Example 8, compound 17 was prepared from 2,4-difluorobenzenecarbothioamide (3.46 g, 20 mol; obtained as described in the literature—see Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-5330), NaH (0.48 g, 20 mmol, 60% suspension in mineral oil), and carbon disulfide (3.35 g, 44 mmol) in 42% yield.

Example 19

5-(2,4,6-Trichlorophenyl)-3H-1,2,4-dithiazol-3-thione (18)

Following the procedure described in Example 8, compound 18 was prepared from 2,4,6-trichlorobenzenecarbothioamide (4.81 g, 20 mol; obtained as described in the literature see Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-5330), NaH (0.48 g, 20 mmol, 60% suspension in mineral oil), and carbon disulfide (3.35 g, 44 mmol) in 44% yield.

Example 20

5-(2,4,6-Trifluorophenyl)-3H-1,2,4-dithiazol-3-thione (19)

Following the procedure described in Example 8, compound 19 was prepared from 2,4,6-trifluorobenzenecarboth-ioamide (3.82 g, 20 mol; obtained as described in the literature—see Crane, L. J.; Anastassiadou, M.; Stigliani, J.-L.; Baziard-Mouysset, G.; Payard, M. Reactions of some ortho and para halogenated aromatic nitriles with ethylenediamine: selective synthesis of imidazolines. *Tetrahedron* 2004, 25, 5325-5330), NaH (0.48 g, 20 mmol, 60% suspension in mineral oil), and carbon disulfide (3.35 g, 44 mmol) in 49% yield.

Example 21

Solubility of Compound 1 in Organic Solvents

Solubility of compound 1 in mixtures of pyridine with acetonitrile (MeCN) or tetrahydrofuran (THF) was determined by dissolving an aliquot of the compound in a calculated amount of warm pyridine (Py) followed by adding the respective amount of MeCN or THF. The solutions were kept at 20° C. for 24 h, after which time no crystallization of compound 1 was observed. Some useful compositions are:
0.1 Min Py;
0.02 M in THF;
Mixtures of pyridine and MeCN:
0.06 M in Py-MeCN (50:50);
0.05 M in Py-MeCN (40:60);
0.03 M in Py-MeCN (30:70); and
0.02 M in Py-MeCN (20:80);
Mixtures of pyridine and THF:
0.1 M in Py-THF (40:60); and
0.05 M in Py-MeCN (20:80).

Solubility of compound 1 in dimethylformamide (DMF) and N,N-dimethylacetamide was determined by adding the respective solvent, under magnetic stirring, to an aliquot of compound 1 until the mixture became homogeneous. The solutions were kept at 20° C. for 24 h, after which time no crystallization of compound 1 was observed. Under these conditions, compound 1 formed clear saturated solutions at concentrations of 0.12 and 0.13 M in DMF and N,N-dimethylacetamide, respectively.

Example 22

Synthesis of Dinucleotide Phosphorothioate Dimer, 5'-O-(4,4'-dimethoxytrityl)dithymidilyl 2-cyanoethyl phosphorothioate (10)

A solution of commercial 2-cyanoethyl 5'-O-(4,4'-dimethoxytrityl)thymidine 3'-O—(N,N-diisopropyl)phosphoramidite 6 (2.23 g, 3.0 mmol, Glen Research, Sterling, Va.), thymidine-3'-O-levulinate 8 (1.02 g, 3.0 mmol, prepared as disclosed in Kumar, G.; Poonian, M. S. Improvements in oligodeoxyribonucleotide synthesis: methyl N,N-dialkylphosphoramidite dimer units for solid support phosphite methodology. *J. Org. Chem.* 1984, 49(25), 4905-12), and 0.4 M 1H-tetrazole in MeCN (15 mL) was stirred for 45 min. Saturated aqueous $NaHCO_3$ (30 mL) was added, and the mixture was extracted with $CH_2Cl_2$ (3×75 mL). The extracts were dried over $Na_2SO_4$ and evaporated in vacuo, the residual oil was dried on an oil pump. A portion of the material obtained (2.36 g, 2.40 mmol) was dissolved in pyridine (15 mL) and treated with N'-(3H-1,2,4-dithiazole-3-thione-5-yl)-N,N-dimethylmethanimidamide 1 (0.59 g, 2.88 mmol) at room temperature. The reaction was monitored by $^{31}P$ NMR and found to be complete in 10 min.

Acetic acid (1.14 g, 19 mmol) and hydrazine hydrate (380 mg, 7.6 mmol) were added, and the reaction mixture was left overnight. Saturated aqueous $NaHCO_3$ (100 mL) was added, and the mixture was extracted with $CH_2Cl_2$ (3×75 mL). The extracts were dried over Na$_2$SO$_4$ and evaporated in vacuo, the residual oil was dried on an oil pump to give 1.74 g (99%) of the crude dinucleotide phosphorothioate. $^{31}$P NMR, ppm (CD$_3$CN-Py-d$_5$): 70.87 (10, Rp-diastereomer, 45.2%); 70.80 (10, Sp-diastereomer, 54.1%); 1.69 (P=O, 0.7%). An aliquot of this mixture was dissolved in 30% aqueous MeCN and analyzed by reverse-phase HPLC. HPLC analysis was carried out on a Waters Exterra C18 column, 3.5 µm (4.6×100 mm) using 0.05 M aqueous NH$_4$OAc as Buffer A, CH$_3$CN as Buffer B, a linear gradient from 30 to 60% B over a period of 30 min at a flow rate 1.0 mL/min. the Rp and Sp diastereomers of 10 were eluted at retention times 28.6 and 29.12 min, respectively. The P=O dimer (0.4%) was eluted at a retention time of 26.5 min.

Example 23

Figure 5:
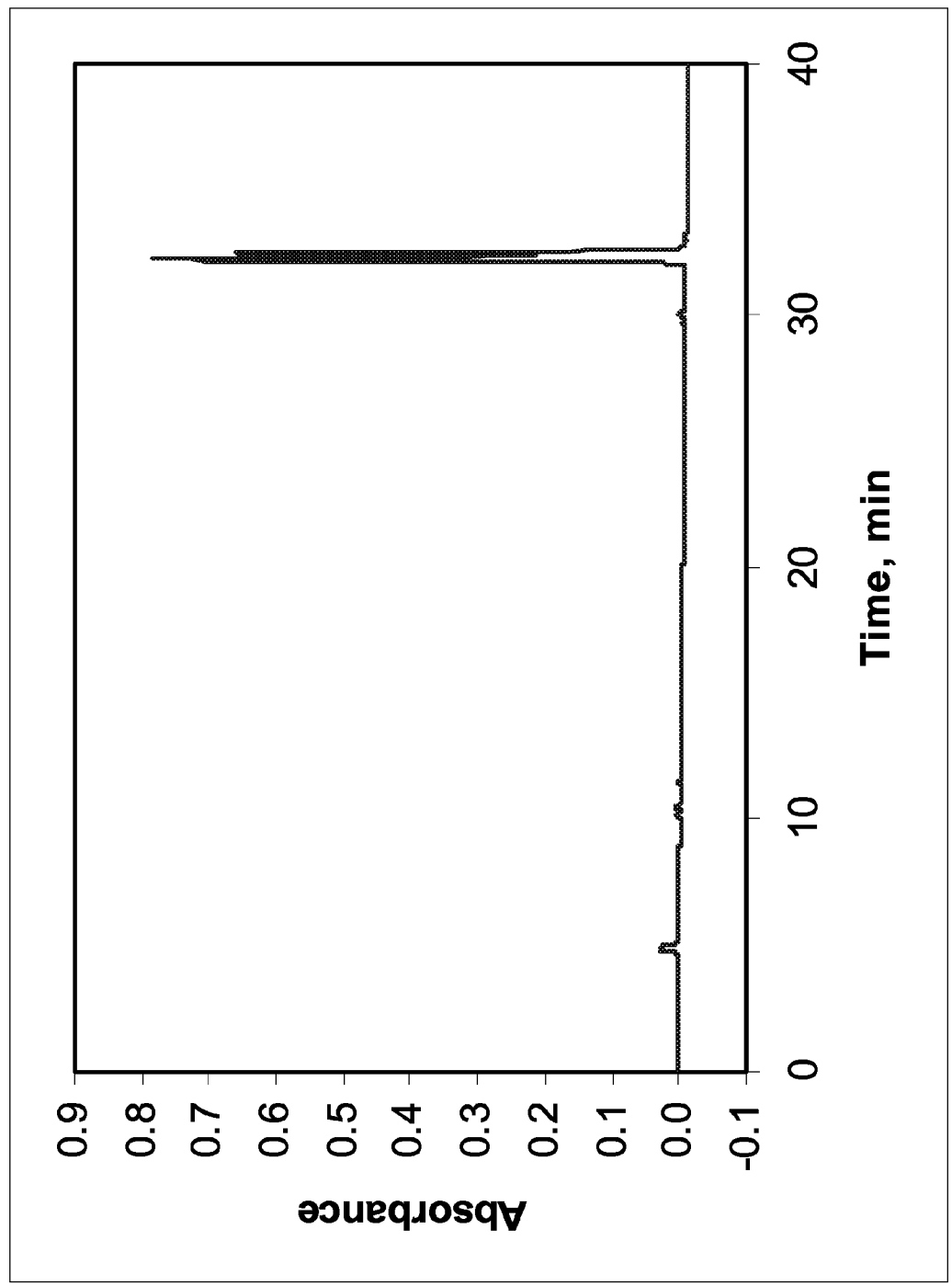
FIG. 5 shows a HPLC profile of crude DMT-T2 phosphorothioate synthesized on solid phase using Compound 1 as a sulfur transfer agent.

Synthesis of Dinucleotide Phosphorothioate Dimer, 5'-O-(4,4'-Dimethoxytrityl)Dithymidilyl Phosphorothioate on Solid Phase DMT-T CPG 500 (1034 g, 87.9 mmol) was detritylated by treating with dichloroacetic acid (3% in DCM) and was washed 3 times with MeCN. The solid support was suspended in a solution of 1H-tetrazole (98.5 g in MeCN (3 L), and DMT-T 2-cyanoethyl phosphoramidite (262.8 g, 351.5 mmol) was added as a solution in MeCN (700 mL). The mixture was stirred for 15 min, and the solid phase was filtered off and washed 3 times with MeCN. The solid phase was then added to a solution of compound 1 (72.2 g, 351.5 mmol) in pyridine (4.4 L), and the suspension obtained was stirred for 10 min. The solid phase was filtered off, washed twice with DMF and 3 times with MeCN and dried in vacuo. An aliquot of the support-bound dimer (2 mmol) was released from the solid phase by treating with conc. aqueous ammonium hydroxide for 2 h at room temperature. The solution obtained was evaporated in vacuo, the residue was dissolved in 30% aqueous MeCN and analyzed by reverse-phase HPLC. HPLC analysis was carried out on a Zorbax 300SB C8 column, 3.5 µm (4.6×150 mm) using 0.1 M aqueous NH$_4$OAc as Buffer A, 80% aqueous CH$_3$CN as Buffer B, and a linear gradient from 0 to 60% B over a period of 40 min at a flow rate of 1.0 mL/min (FIG. 5). The crude deprotection mixture contained 5'-O-(4,4'-dimethoxytrityl)dithymidilyl phosphorothioate and 5'-O-(4,4'-dimethoxytrityl)dithymidilyl phosphate in a ratio of 99.8:0.2.

Example 24

Figure 6:
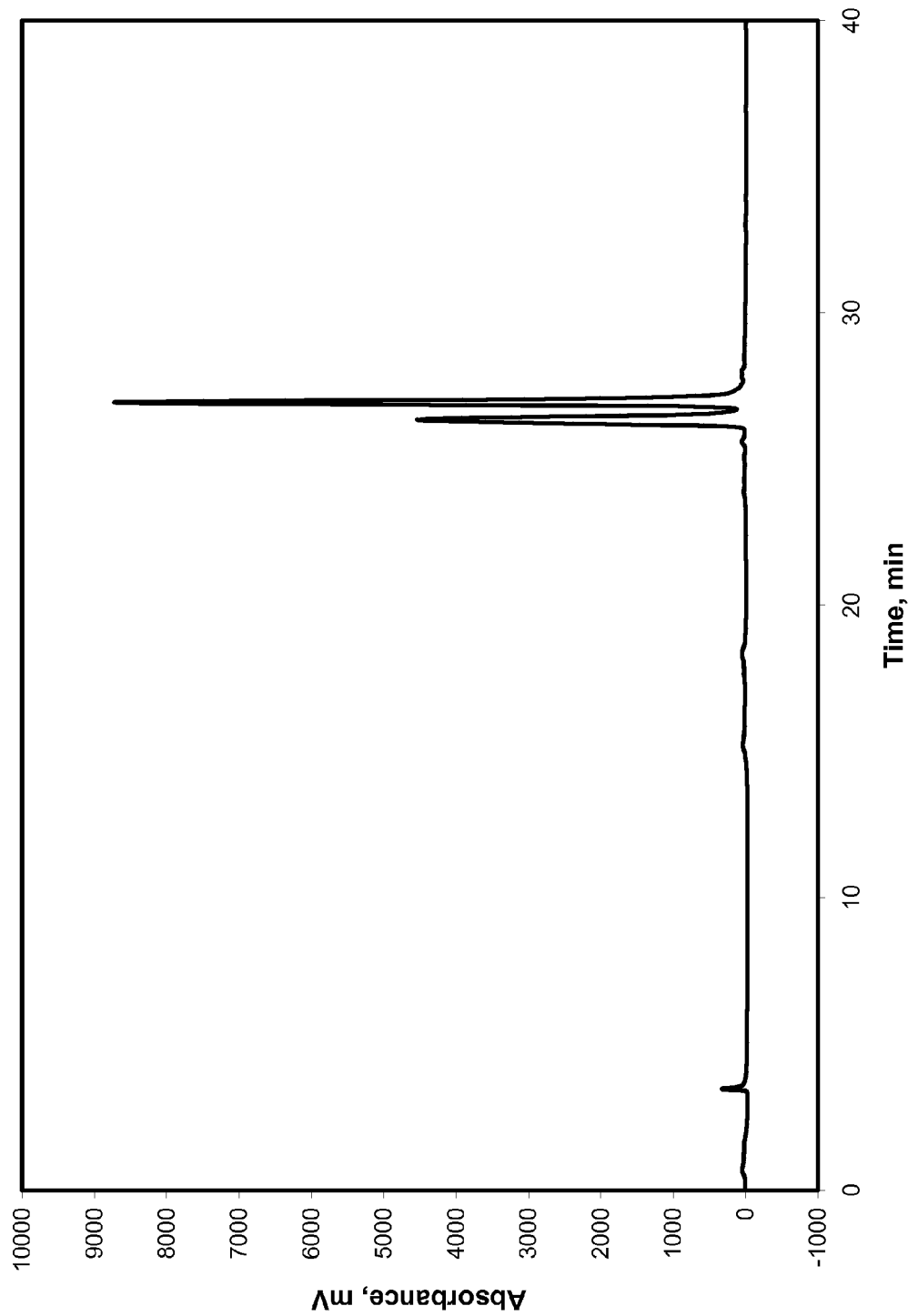
FIG. 6 shows the HPLC of DMT-T$_{10}$ phosphorothioate (SEQ ID NO:1) synthesized using Compound 1 as a sulfur transfer agent.

Synthesis of DMT-T$_{10}$ Phosphorothioate (SEQ ID NO: 1) Using Compound 1 as a Sulfurizing Agent The 2'-deoxyoligonucleotide was assembled on an Applied Biosystems DNA/RNA synthesizer 380B on a 0.2 µmol scale starting with a commercial DMT-dT-Succinyl-CPG (500 A, Glen Research, Sterling, Va.), using 0.1 M solutions of protected nucleoside phosphoramidites (Glen Research, Sterling, Va.), and the following standard protocol of the chain assembly for oligonucleotide phosphorothioates:

Compound 1 was dissolved in mixtures of pyridine and CH$_3$CN at 0.02-0.05 M concentration. Sulfurization was carried out by delivering 4 equiv of Compound 1 to columns followed by a waiting period of 1 to 5 min. Under the optimized conditions, the complete sulfur transfer using 0.02, 0.05, and 0.1 M solutions of Compound 1 requires contact times of 2, 1, and 0.5 min, respectively. The final deprotection was carried out by treating the solid supports with concentrated aqueous ammonium hydroxide (2 mL) for 3 h at room temperature. Upon evaporation in vacuo, the crude deprotection mixtures were dissolved in water, filtered, and analyzed by ES MS and reverse-phase HPLC. HPLC analysis was carried out on Waters Delta Pak C18 column, (3.9×300 mm) using 0.1 M aqueous NH$_4$OAc as Buffer A, 80% aqueous CH$_3$CN as Buffer B, and a linear gradient from 0 to 60% B over a period of 40 min at a flow rate of 1.5 mL/min (FIG. 6). ES MS: 3426.3 (observed), 3426.9 (calculated).

Example 25

Synthesis of DMT-d(TAG TGA AGT ACA CTA TGA TGT) Phosphorothioate (SEQ ID NO: 2)

Figure 7:
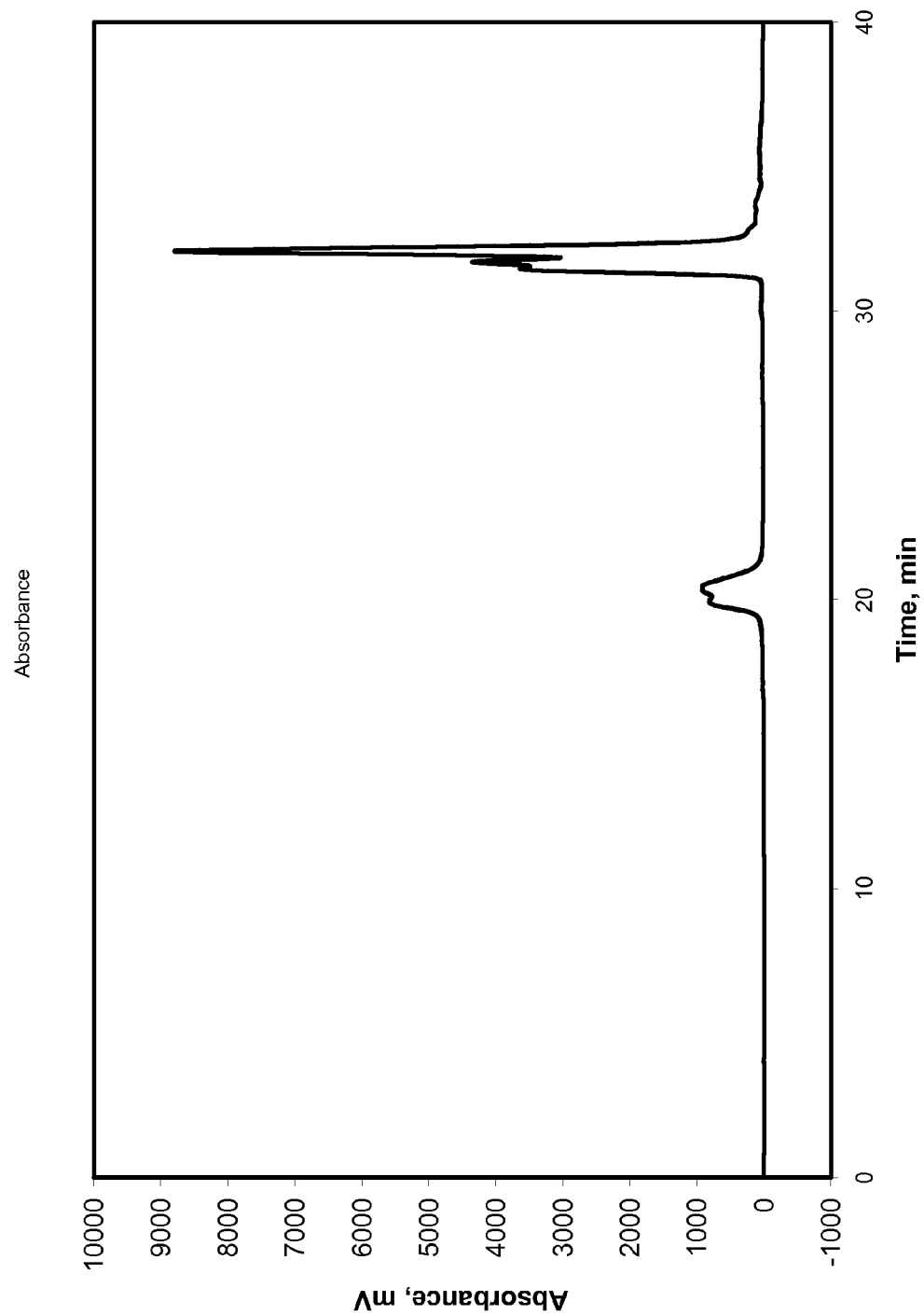
FIG. 7 shows the HPLC of DMT-d(5'-TGT GAG TAC CAC TGA TTC-3') phosphorothioate (SEQ ID NO:2) synthesized using Compound 1 as a sulfur transfer agent.
Figure 8:
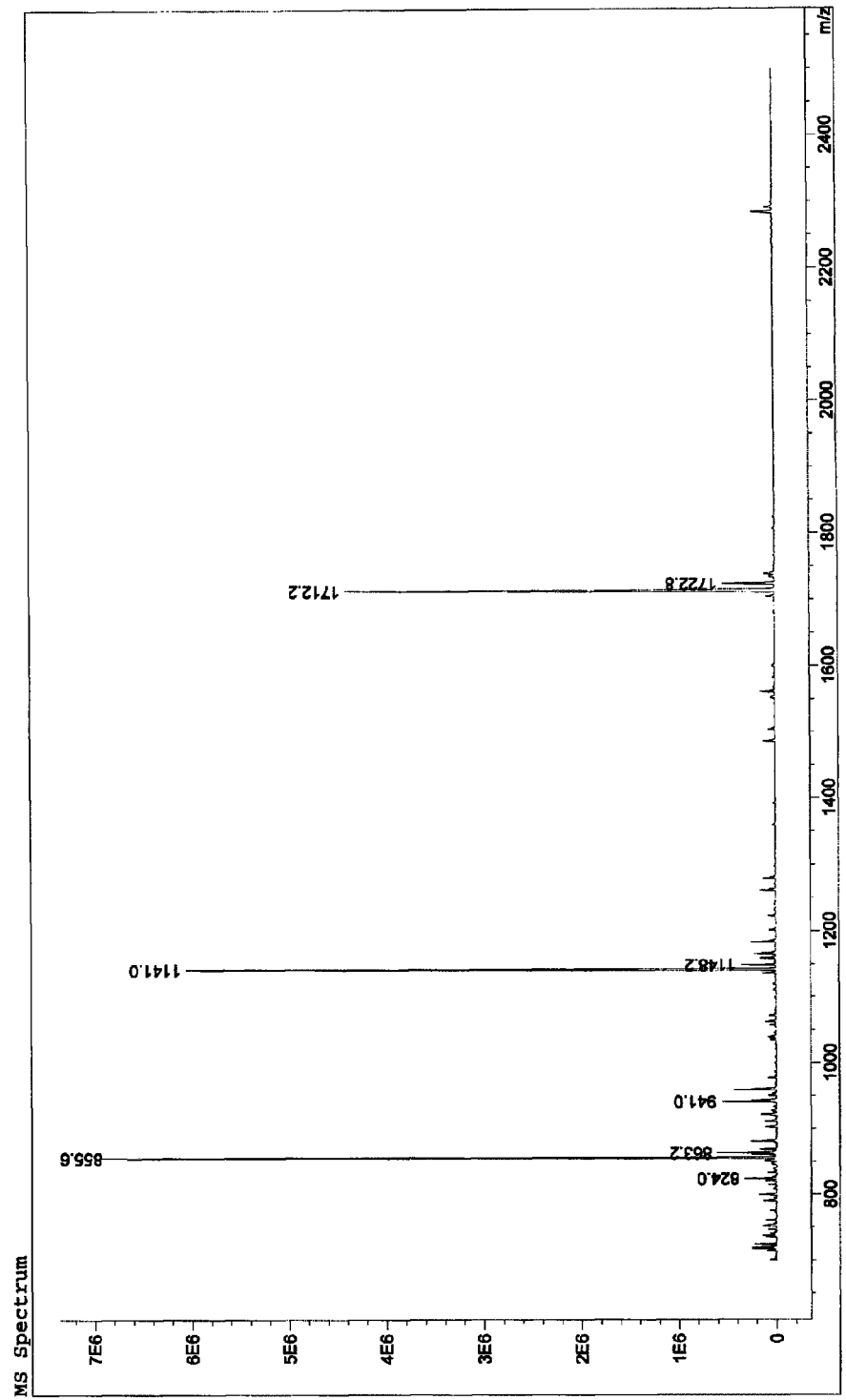
FIG. 8 shows ES MS of DMT-T$_{10}$ phosphorothioate (SEQ ID NO:1) synthesized using Compound 1 as a sulfur transfer agent.
Figure 9:
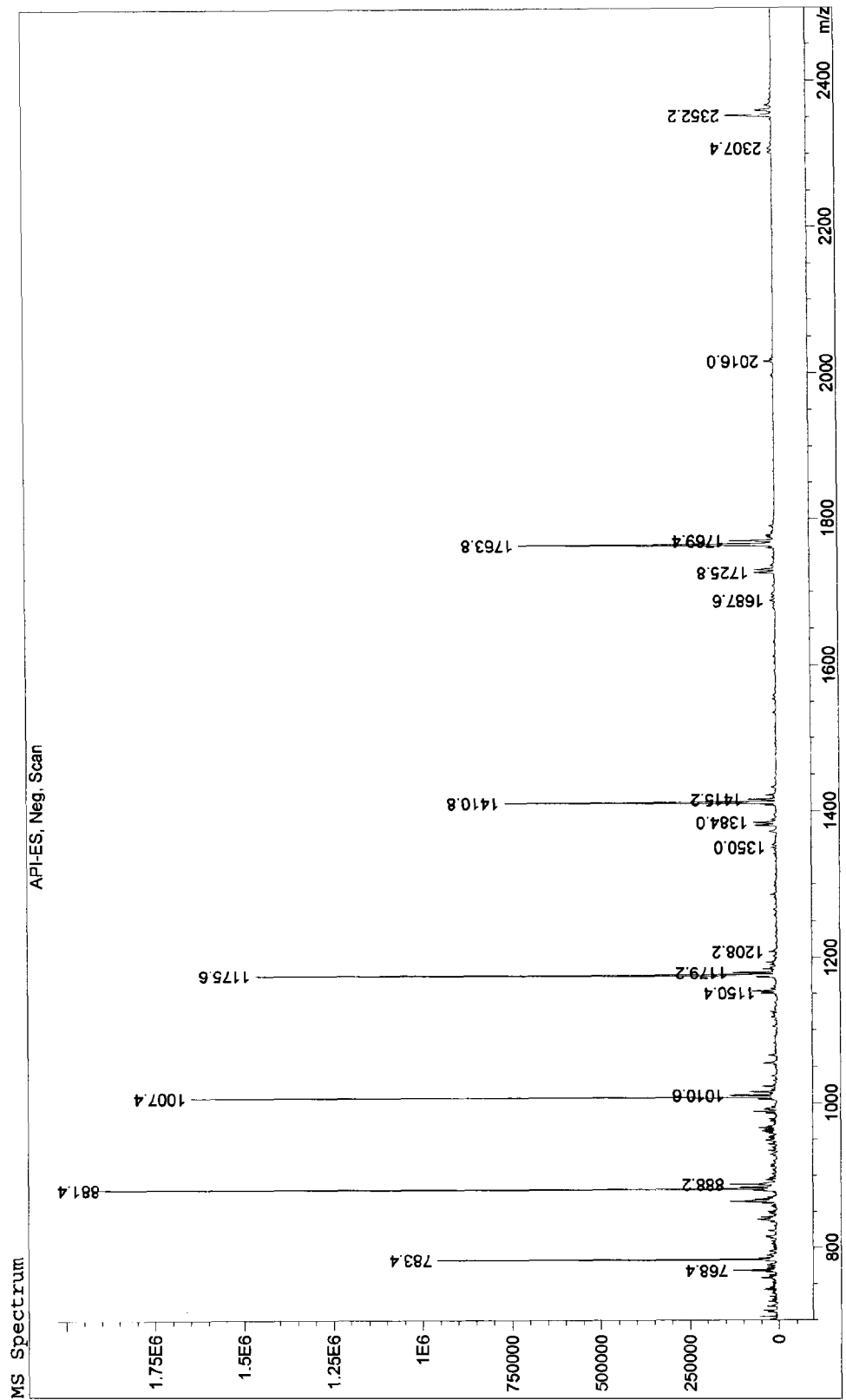
FIG. 9 shows ES MS of DMT-d(5'-TGT GAG TAC CAC TGA TTC-3') phosphorothioate (SEQ ID NO:2) synthesized using Compound 1 as a sulfur transfer agent.

The 2'-deoxyoligonucleotide was assembled on an Applied Biosystems DNA/RNA synthesizer 380B on a 0.2 µmol scale starting with a commercial DMT-dT-Succinyl-CPG (500 A, Glen Research, Sterling, Va.), using 0.1 M solutions of protected nucleoside phosphoramidites (Glen Research, Sterling, Va.), and the standard protocol of the chain assembly for oligonucleotide phosphorothioates. Sulfurization was carried out by delivering 4 equiv of a 0.02 M solution of Compound 1 to columns followed by a waiting period for 2 min. The final cleavage and deprotection of nucleic bases was carried out by treating the solid supports with concentrated aqueous ammonium hydroxide (2 mL) at 65° C. for 8 h. Upon evaporation in vacuo, the crude deprotection mixtures were dissolved in water, filtered, and analyzed by ES MS and reverse-phase HPLC. HPLC analysis was carried out on Waters Delta Pak C18 column, (3.9×300 mm) using 0.1 M aqueous NH$_4$OAc as Buffer A, 80% aqueous CH$_3$CN as Buffer B, and a linear gradient from 0 to 60% B over a period of 40 min at a flow rate of 1.5 mL/min (FIG. 7). ES MS: 7059.2 (observed), 7059.7 (calculated).

Example 26

Synthesis of DMT-(U$^{OMe}$G$^{OMe}$U$^{OMe}$ G$^{OMe}$A$^{OMe}$G TdAdC dCdAdC TG$^{OMe}$A$^{OMe}$ U$^{OMe}$U$^{OMe}$C$^{OMe}$) Phosphorothioate (SEQ ID NO: 3)

Following the procedure described in Example 25, the title oligonucleotide wherein A$^{OMe}$, G$^{OMe}$, C$^{OMe}$, and U$^{OMe}$ refer to the respective 2'-O-methylribonucleotide residues and dA, dG, dC, and T refer to the respective 2'-deoxynucleotide residues, was synthesized. Sulfurizing reagent 1 was dissolved in pyridine at 0.1 M concentration. Sulfurization was carried out by delivering 4 equiv of sulfurizing reagent 1 to columns followed by a waiting period for 5 min. The final cleavage and deprotection of nucleic bases was carried out by treating the solid supports with concentrated aqueous ammonium hydroxide (2 mL) at 65° C. for 8 h. Upon evaporation in vacuo, the crude deprotection mixtures were dissolved in water, filtered, and analyzed by ES MS and reverse-phase HPLC. HPLC analysis was carried out on Waters Delta Pak C18 column, (3.9×300 mm) using 0.1 M aqueous NH$_4$OAc as Buffer A, 80% aqueous CH$_3$CN as Buffer B, and a linear gradient from 0 to 60% B over a period of 40 min at a flow rate of 1.5 mL/min. ES MS: 6309.8 (observed), 6309.20 (calculated).

Example 27

Synthesis of UGU GAG UAC CAC UGA UUC Phosphorothioate (SEQ ID NO: 4)

Following the procedure described in Example 25, the title oligonucleotide wherein A, G, C, and U refer to the respective ribonucleotide residues was synthesized using ethylthiotetrazole as an activator. Sulfurizing reagent 1 was dissolved in pyridine at 0.1 M concentration. Sulfurization was carried out by delivering 4 equiv of sulfurizing reagent 1 to columns followed by a waiting period for 3 min. The release from the solid phase and deprotection of nucleic bases were carried out as disclosed in N. Usman, K. K. Ogilvie, M.-Y. Jiang, and R. J. Cedergren, J. Am. Chem. Soc. 1987, 109, 7845-7854, which is incorporated by reference herein in its entirety. The removal of 2'-O-tBDMS groups was carried out as disclosed in Q. Song, R. A. Jones. Use of silyl ethers as fluoride ion scavengers in RNA synthesis. *Tetrahedron Lett.* 1999, 40, 4653-4654, which is incorporated by reference herein in its entirety. The crude deprotection mixture was analyzed by ES MS and ion-exchange HPLC. HPLC analysis was carried out on a Dionex DNAPac PA200 column (4×250 mm) using 0.1 M aqueous Na phosphate, pH 8.5 as Buffer A,) 0.1 M aqueous Na phosphate plus 1 M NaBr, pH 8.5 as Buffer B, and a linear gradient from 0 to 60% B over a period of 40 min at a flow rate of 1.5 mL/min. ES MS: 5965.9 (observed), 5966.5 (calculated).

Example 28

Stability of N'-(3-Thioxo-3H-1,2,4-Dithiazol-5-Yl)-N,N-Dimethylmethanimidamide 1 in Solution Stability studies were carried out by keeping a 0.02 M solution of compound 1 in anhydrous pyridine-$CH_3CN$ (20:80) at 25° C. Every two weeks, the solution was used as the sulfurizing reagent in the preparation of DMT-T10 phosphorothioate (SEQ ID NO: 1). Upon completion of the synthesis, the solid phase-bound material was released with concentrated aqueous ammonium hydroxide for 2 h, the solution was evaporated, and the crude oligonucleotide obtained was re-dissolved in water and analyzed by reverse-phase HPLC (FIG. 6). Comparison of the HPLC traces showed no deterioration of the activity of the reagent over a period of 20 weeks, at which point the experiment was terminated.

Example 29

Synthesis of DMT-$T_{10}$ Phosphorothioate (SEQ ID NO: 1) Using Compound 7 as a Sulfurizing Agent Following the procedure described in Example 25, the title oligonucleotide was synthesized. Sulfurizing reagent 7 was dissolved in $CH_3CN$ at 0.02-0.1 M concentration. Under the optimized conditions, the complete sulfur transfer using 0.02, 0.05, and 0.1 M solutions of 7 required the contact time of 2, 1, and 0.5 min, respectively. The final deprotection was carried out by treating the solid supports with concentrated aqueous ammonium hydroxide (2 mL) for 3 h at room temperature. Upon evaporation in vacuo, the crude deprotection mixtures were dissolved in water, filtered, and analyzed by ES MS and reverse-phase HPLC. HPLC analysis was carried out on Waters Delta Pak C18 column, (3.9×300 mm) using 0.1 M aqueous $NH_4OAc$ as Buffer A, 80% aqueous $CH_3CN$ as Buffer B, and a linear gradient from 0 to 60% B over a period of 40 min at a flow rate of 1.5 mL/min. ES MS: 3426.5 (observed), 3426.9 (calculated).

Example 30

Synthesis of DMT-$T_{10}$ Phosphorothioate (SEQ ID NO: 1) Using Compound 12 as a Sulfurizing Agent Following the procedure described in Example 25, the title oligonucleotide was synthesized. Sulfurizing reagent 12 was dissolved in $CH_3CN$ at 0.02-0.1 M concentration. Under the optimized conditions, the complete sulfur transfer using 0.02, 0.05, and 0.1 M solutions of 12 required the contact time of 2, 1, and 0.5 min, respectively. The final deprotection was carried out by treating the solid supports with concentrated aqueous ammonium hydroxide (2 mL) for 3 h at room temperature. Upon evaporation in vacuo, the crude deprotection mixtures were dissolved in water, filtered, and analyzed by ES MS and reverse-phase HPLC. HPLC analysis was carried out on Waters Delta Pak C18 column, (3.9×300 mm) using 0.1 M aqueous $NH_4OAc$ as Buffer A, 80% aqueous $CH_3CN$ as Buffer B, and a linear gradient from 0 to 60% B over a period of 40 min at a flow rate of 1.5 mL/min. ES MS: 3426.2 (observed), 3426.9 (calculated).

Example 31

Synthesis of DMT-$T_{10}$ Phosphorothioate (SEQ ID NO: 1) Using Compound 17 as a Sulfurizing Agent Following the procedure described in Example 25, the title oligonucleotide was synthesized. Sulfurizing reagent 17 was dissolved in $CH_3CN$ at 0.02-0.1 M concentration. Under the optimized conditions, the complete sulfur transfer using 0.02, 0.05, and 0.1 M solutions of 17 required the contact time of 2, 1, and 0.5 min, respectively. The final deprotection was carried out by treating the solid supports with concentrated aqueous ammonium hydroxide (2 mL) for 3 h at room temperature. Upon evaporation in vacuo, the crude deprotection mixtures were dissolved in water, filtered, and analyzed by ES MS and reverse-phase HPLC. HPLC analysis was carried out on Waters Delta Pak C18 column, (3.9×300 mm) using 0.1 M aqueous $NH_4OAc$ as Buffer A, 80% aqueous $CH_3CN$ as Buffer B, and a linear gradient from 0 to 60% B over a period of 40 min at a flow rate of 1.5 mL/min. ES MS: 3426.7 (observed), 3426.9 (calculated).

Example 32

Synthesis of DMT-$T_{10}$ Phosphorothioate (SEQ ID NO: 1) Using Compound 18 as a Sulfurizing Agent Following the procedure described in Example 25, the title oligonucleotide was synthesized. Sulfurizing reagent 18 was dissolved in $CH_3CN$ at 0.02-0.1 M concentration. Under the optimized conditions, the complete sulfur transfer using 0.02, 0.05, and 0.1 M solutions of 18 required the contact time of 2, 1, and 0.5 min, respectively. The final deprotection was carried out by treating the solid supports with concentrated aqueous ammonium hydroxide (2 mL) for 3 h at room temperature. Upon evaporation in vacuo, the crude deprotection mixtures were dissolved in water, filtered, and analyzed by ES MS and reverse-phase HPLC. HPLC analysis was carried out on Waters Delta Pak C18 column, (3.9×300 mm) using 0.1 M aqueous $NH_4OAc$ as Buffer A, 80% aqueous $CH_3CN$ as Buffer B, and a linear gradient from 0 to 60% B over a period of 40 min at a flow rate of 1.5 mL/min. ES MS: 3426.0 (observed), 3426.9 (calculated).

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having the general structure according to Formula I:

Formula I:

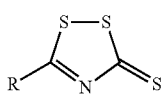

wherein:

R is $-N=C(H)-N(R^1)(R^2)$, $-C_6H_4-R^3$, $-C_6H_3(R^3)(R^4)$; or $-C_6H_2(R^3)(R^4)(R^5)$;

$R^1$ and $R^2$ are independently H, an alkyl group, an aryl group, or an aralkyl group, or $R^1$ and $R^2$ combined form a $-(CH_2)_n-$, wherein n varies from 2 up to about 20, thereby forming a ring structure containing the N to which they are attached, or $R^1+R^2$ combined form the linkage $-(CH_2)_{n'}-X-(CH_2)_{n''}-$, wherein n' and n" independently vary from 2 to about 20, and X is O, NR or S, provided, however, that the total of n' and n" does not exceed 24, and $R^3$, $R^4$ and $R^5$ are independently an alkyl group, an aryl group, an alkoxy group, an aryloxy group, or a halogen atom, provided, however, that when R is $-C_6H_4-R^3$, $R^3$ is not 2-chloro or 4-chloro, or when R is $-C_6H_3(R^3)(R^4)$, and $R^3$ and $R^4$ are positioned in a 2,4-orientation, $R^3$ and $R^4$ are, not both chloro, provided, however, that when R of Formula I is $-N=C(H)-N(R^1)(R^2)$, $R^1$ and $R^2$ are not both $CH_3$ or $C_2H_5$.

2. The compound of claim 1 wherein R of Formula I is $-N=C(H)-N(R^1)(R^2)$, and $R^1$ and $R^2$ are n-butyl, such that R is $-N=C(H)-N(C_4H_9)_2$.

3. The compound of claim 1 wherein R is —N=C(H)—N($R^1$)($R^2$), and $R^1+R^2$ is —($CH_2$)$_2$—O—($CH_2$)$_2$—.

4. The compound of claim 1 wherein R is —N=C(H)—N($R^1$)($R^2$), and $R^1+R^2$—($CH_2$)$_4$—.

5. The compound of claim 1 wherein R of Formula I is $C_6H_4$-4-$CH_3$.

6. The compound of claim 1 wherein R of Formula I is $C_6H_4$-4-$OCH_3$.

7. The compound of claim 1 wherein R of Formula I is $C_6H_4$-3-Cl.

8. The compound of claim 1 wherein R of Formula I is $C_6H_4$-2-F.

9. The compound of claim 1 wherein R of Formula I is $C_6H_4$-3-F.

10. The compound of claim 1 wherein R of Formula I is $C_6H_4$-4-F.

11. The compound of claim 1 wherein R of Formula I is $C_6H_3$-2,6-$Cl_2$.

12. The compound of claim 1 wherein R of Formula I is $C_6H_3$-2,4-$F_2$.

13. The compound of claim 1 wherein R of Formula I is $C_6H_3$-2,6-$F_2$.

14. The compound of claim 1 wherein R of Formula I is $C_6H_2$-2,4,6-$Cl_3$.

15. The compound of claim 1 wherein R of Formula is $C_6H_2$-2,4,6-$F_3$.

16. A process of sulfur transfer that comprises bringing an oligonucleotide having at least one reactive internucleosidic linkage that contains a phosphorous (III) atom in contact with a sulfur transfer reagent of Formula III for a time sufficient for the transfer of sulfur from said reagent to said reactive internucleosidic linkage, wherein Formula III has the structure:

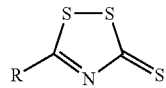

wherein:
R is H, —N=C(H)—N($R^1$)($R^2$), —$C_6H_4$—$R^3$, —$C_6H_3$($R^3$)($R^4$); or —$C_6H_2$($R^3$)($R^4$)($R^5$);

$R^1$ and $R^2$ are independently H, an alkyl group, an aryl group, or an aralkyl group, or $R^1$ and $R^2$ combined form a —($CH_2$)$_n$—, wherein n varies from 2 up to about 20, thereby forming a ring structure containing the N to which they are attached, or $R^1+R^2$ combined form the linkage —($CH_2$)$_{n'}$—X—($CH_2$)$_{n''}$—, wherein n' and n" independently vary from 2 to about 20, and X is O, NR or S, provided, however, that the total of n' and n" does not exceed 24, and $R^3$, $R^4$ and $R^5$ are independently H, an alkyl group, an an group, an alkoxy group, an aryloxy group, or a halogen atom, provided, however, that when R of Formula III is —N=C(H)—N($R^1$)($R^2$), $R^1$ and $R^2$ are not both $CH_3$ or $C_2H_5$.

17. The process according to claim 16, wherein said oligonucleotide contains 2'-deoxynucleoside, 2'-O-alkylribonucleoside, 2'-O-protected ribonucleoside, LNA nucleoside residues, or combinations of any two or more thereof.

18. The process according to claim 16, wherein said reactive internucleoside linkage is a phosphite, alkylphosphite, thiophosphite, methylphosphonate, H-phosphonate, or H-phosphonothioate internucleosidic linkage.

19. The process according to claim 16 wherein said oligonucleotide is attached to a solid phase material.

\* \* \* \* \*